US007605131B2

(12) United States Patent (10) Patent No.: US 7,605,131 B2
Mano et al. (45) Date of Patent: Oct. 20, 2009

(54) EML4-ALK FUSION GENE

(75) Inventors: Hiroyuki Mano, Tokyo (JP); Sadao Kuromitsu, Tokyo (JP); Nobuaki Shindo, Tokyo (JP); Takatoshi Soga, Tokyo (JP); Takashi Furutani, Tokyo (JP)

(73) Assignees: Astellas Pharma Inc., Tokyo (JP); CureGene K.K., Tokyo (JP)

( * ) Notice: Subject to any disclaimer, the term of this patent is extended or adjusted under 35 U.S.C. 154(b) by 0 days.

(21) Appl. No.: 12/100,595

(22) Filed: Apr. 10, 2008

(65) Prior Publication Data
US 2009/0099193 A1 Apr. 16, 2009

(30) Foreign Application Priority Data
Oct. 11, 2007 (EP) ................................. 07254044
Oct. 11, 2007 (JP) ............................. 2007-265917

(51) Int. Cl.
*C07H 21/02* (2006.01)
*A61K 38/17* (2006.01)
(52) U.S. Cl. ....................................... 514/12; 536/23.1
(58) Field of Classification Search ................... 514/12; 536/23.1
See application file for complete search history.

(56) References Cited
U.S. PATENT DOCUMENTS
2008/0090776 A1 4/2008 Mano et al.

FOREIGN PATENT DOCUMENTS

| WO | 2004/080980 A1 | 9/2004 |
| WO | 2005/009389 A2 | 2/2005 |
| WO | 2005/016894 A1 | 2/2005 |
| WO | 2005/097765 A1 | 10/2005 |
| WO | 2008/127248 A1 | 10/2008 |

OTHER PUBLICATIONS

Willy G. Dirks, et al.; "Expression and Functional Analysis of the Anaplastic Lymphoma Kinase (*ALK*) Gene in Tumor Cell Lines"; International Journal of Cancer; 2002; pp. 49-56; vol. 100; Wiley-Liss, Inc.
Stephan W. Morris, et al.; "Fusion of a Kinase Gene, *ALK*, to a Nucleolar Protein Gene, *NPM*, in Non-Hodgkin's Lymphoma"; Science; Mar. 4, 1994; pp. 1281-1284; vol. 263.
Mami Shiota, et al.; "Anaplastic Large Cell Lymphomas Expressing the Novel Chimeric Protein p80$^{NPM/ALK}$: A Distinct Clinicopathologic Entity"; Blood; Sep. 1, 1995; pp. 1954-1960; vol. 86, No. 5.
Christian Touriol, et al.; "Further Demonstration of the Diversity of Chromosomal Changes Involving 2p23 in ALK-positive Lymphoma: 2 Cases Expressing ALK Kinase Fused to CLTCL (clathrin chain polypeptide-like)"; Blood; May 15, 2000; pp. 3204-3207; vol. 95, No. 10.

Luis Hernandez, et al.; "*TRK*-Fused Gene (TFG) is a New Partner of *ALK* in Anaplastic Large Cell Lymphoma Producing Two Structurally Different *TFG-ALK* Translocations"; Blood; Nov. 1, 1999; pp. 3265-3268; vol. 94, No. 9.
Larisa V. Debelenko, et al.; "Identification of *CARS-ALK* Fusion in Primary and Metastatic Lesions of an Inflammatory Myofibroblastic Tumor"; Laboratory Investigation; Sep. 2003; pp. 1255-1265; vol. 83, No. 9.
Ioannis Panagopoulus, et al.; "Fusion of the *SEC31L1* and *ALK* Genes in an Inflammatory Myofibroblastic Tumor"; International Journal of Cancer; 2006; pp. 1181-1186; vol. 118.
Roberto Piva, et al.; "Ablation of Oncogenic ALK is a Viable Therapeutic Approach for Anaplastic Large-cell Lymphomas"; Blood; Jan. 15, 2006; pp. 689-697; vol. 107, No. 2.
Rongshi Li, et al.; "Design and Synthesis of 5-Aryl-pyridone-carboxamides as Inhibitors of Anaplastic Lymphoma Kinase"; Journal of Medicinal Chemistry; 2006; pp. 1006-1015; vol. 49, No. 3.
Virginie Lacronique, et al.; "A TEL-JAK2 Fusion Protein with Constitutive Kinase Activity in Human Leukemia"; Science; Nov. 14, 1997; pp. 1309-1312; vol. 278.
Toshinori Iwahara, et al. "Molecular Characterization of ALK, a Receptor Tyrosine Kinase Expressed Specifically in the Nervous System"; Oncogene; Jan. 30, 1997; pp. 439-449; vol. 14; Stockton Press.
Luis Hernandez, et al.; "Diversity of Genomic Breakpoints in *TFG-ALK* Translocations in Anaplastic Large Cell Lymphomas"; American Journal of Pathology; Apr. 2002; pp. 1487-1494; vol. 160, No. 4.
Brandon Lawrence, et al.; "*TPM3-ALK* and *TPM4-ALK* Oncogenes in Inflammatory Myofibroblastic Tumors"; American Journal of Pathology; Aug. 2000; pp. 377-384; vol. 157, No. 2.
Martin U. Kuefer, et al.; "Retrovirus-Mediated Gene Transfer of *NPM-ALK* Causes Lymphoid Malignancy in Mice"; Blood; Oct. 15, 1997; pp. 2901-2910; vol. 90, No. 8.
Gisele W. B. Colleoni, et al.; "*ATIC-ALK*: A Novel Variant *ALK* Gene Fusion in Anaplastic Large Cell Lymphoma Resulting From the Recurrent Cryptic Chromosomal Inversion, inv(2)(p23q35)"; American Journal of Pathology; Mar. 2000; pp. 781-789; vol. 156, No. 3.
Tong Zhu, et al.; "Polymer-Supported Synthesis of Pyridone-Focused Libraries as Inhibitors of Anaplastic Lymphoma Kinase"; Journal of Combinatorial Chemistry; 2006; pp. 401-409; vol. 8, No. 3.
Kojo S.J. Elenitoba-Johnson, et al.; "Proteomic Identification of Oncogenic Chromosomal Translocation Partners Encoding Chimeric Anaplastic Lymphoma Kinase Fusion Proteins"; PNAS; May 9, 2006; pp. 7402-7407; vol. 103, No. 19.
Anna V. Galkin, et al.; "Identification of NVP-TAE684, a Potent, Selective, and Efficacious Inhibitor of NPM-ALK"; PNAS; Jan. 2, 2007; Epub2006 Dec, pp. 270-275; vol. 104, No. 1.
Manabu Soda, et al.; "Retroviral Expression Screening of Oncogenes in Primary Non-small-cell Lung Cancer"; O-324; Proceedings of the 65th Annual Meeting of the Japanese Cancer Association; Issued Aug. 28, 2006.

(Continued)

*Primary Examiner*—Brandon J Fetterolf
(74) *Attorney, Agent, or Firm*—Sughrue Mion, PLLC

(57) ABSTRACT

The present inventors found that a fusion gene present in some cancer patients is an oncogene. The present invention relates to a polypeptide as a novel fusion protein, a polynucleotide encoding the polypeptide, a vector comprising the polynucleotide, a transformed cell comprising the vector, and a therapeutic agent for cancer.

4 Claims, No Drawings

OTHER PUBLICATIONS

Manabu Soda, et al.; "A Novel Transforming Fusion Kinase Identified in Non-small-cell Lung Cancer"; O-455, Proceedings of the 66th Annual Meeting of the Japanese Cancer Association; Issued Aug. 25, 2007.

Hiroyuki Mano; "A Novel Transforming Fusion Kinase in Lung Cancer"; ML10 Proceedings of the 66th Annual Meeting of the Japanese Cancer Association; Issued Aug. 25, 2007.

K. Pulford, et al.; "The Emerging Normal and Disease-related Roles of Anaplastic Lymphoma Kinase"; Cellular and Molecular Life Sciences; 2004; pp. 2939-2953; vol. 61.

Klarisa Rikova, et al.; "Global Survey of Phosphotyrosine Signaling Indentifies Oncogenic Kinases in Lung Cancer"; Dec. 14, 2007; pp. 1190-1203; vol. 131.

Ultan McDermott, et al.; "Identification of Genotype-correlated Sensitivity to Selective Kinase Inhibitors by Using High-throughput Tumor Cell Line Profiling"; PNAS; Dec. 11, 2007; pp. 19936-19941; vol. 104, No. 50.

Jussi P. Koivunen, et al.; "EML4-ALK Fusion Gene and Sensitivity to an ALK Kinase Inhibitor in Lung Cancer"; Proceedings of the American Association for Cancer Research Annual Meeting; #2373; Apr. 2008; vol. 49.

Kim Sungjoon, et al.; "Therapeutic Application of ALK-Specific Inhibitor Against Epithelial Cancer, Including Lung Cancer"; American Association for Cancer Research Annual Meeting Proceedings Supplement: Late-Breaking Abstracts; Poster Section 18; #LB-41; Apr. 2008.

Daisy Wing-Sze Wong, et al.; "*EML4-ALK* is a New Oncogene in Non-small Cell Lung Carcinoma Showing Wild-type *EGFR* and *K-RAS* From Non-smokers"; American Association for Cancer Research Annual Meeting Proceedings Supplement: Late-Breaking Abstracts; Poster Section 19; #LB-62; Apr. 2008.

Sven Perner, et al.; "*EML4-ALK* Fusion Lung Cancer: A Rare Acquired Event"; Neoplasia; Mar. 2008; pp. 298-302; vol. 10, No. 3.

Kazuya Shinmura, et al.; "EML4-ALK Fusion Transcripts, but no NPM-, TPM3-, CLTC-, ATIC-, or TFG-ALK Fusion Transcripts, in Non-small Cell Lung Carcinomas"; Lung Cancer; 2008; pp. 1-7.

Kentaro Inamura, et al.; "EML4-ALK Fusion is Linked to Histological Characteristics in a Subset of Lung Cancers"; Journal of Thoracic Oncology; Jan. 2008; pp. 13-17; vol. 3, No. 1.

Manabu Soda, et al.; "Identification of the Transforming *EML4-ALK* Fusion Gene in Non-small-cell Lung Cancer"; XP-002464689; Nature; Aug. 2, 2007; pp. 561-567; vol. 448, Nature Publishing Group.

Michal Marzec, et al.; "Inhibition of ALK Enzymatic Activity in T-Cell Lymphoma Cells Induces Apoptosis and Suppresses Proliferation and STAT3 Phosphorylation Independently of Jak3"; XP-002464690; Laboratory Investigation; A Journal of Technical Methods and Pathology; Sep. 19, 2005; pp. 1544-1554; vol. 85, No. 12.

K. Pulford, et al.; "Anaplastic Lymphoma Kinase Proteins in Growth Control and Cancer"; XP-002464691; Journal of Cellular Physiology; Jun. 2004; pp. 330-358; vol. 199; No. 3.

Weihua Wan, et al.; "Anaplastic Lymphoma Kinase Activity is Essential for the Proliferation and Survival of Anaplastic Large-cell Lymphoma Cells"; XP-002464692; Blood; Feb. 15, 2006; pp. 1617-1623; vol. 107; No. 4.

Marc Pollmann, et al.; "Human EML4, a Novel Member of the EMAP Family, is Essential for Microtubule Formation"; XP-002464702; Experimental Cell Research; Jul. 8, 2006; pp. 3241-3251; vol. 312, No. 17.

GenBank accession No. NM_019063; Source: http://www.ncbi.nlm.nih.gov/entrez/viewer.fcgi?19923496:NCBI:12636854, Retrieved from NCBI Mar. 25, 2009, published on Genbank Feb. 11, 2008.

GenBank accession No. AB209477; Source: http://www.ncbi.nlm.nih.gov/entrez/viewer.fcgi?db=nuccore&id=62088533, Retrieved from NCBI Mar. 25, 2009, published on Genbank Nov. 17, 2007.

Ioannis Panagopoulos, et al.; "Fusion of the *SEC31L* 1 and *ALK* Genes in an Inflammatory Myofibroblastic Tumor"; International Journal of Cancer; 2006; pp. 1181-1186; vol. 118.

Roberto Piva, et al.; "Ablation of Oncogenic ALK is a Viable Therapeutic Approach for Anaplastic Large-cell Lymphomas"; Blood; Jan. 15, 2006; pp. 689-697; vol. 107, No. 2.

Rongshi Li, et al.; "Design and Synthesis of 5-Aryl-pyridone-carboxamides as Inhibitors of Anaplastic Lymphoma Kinase"; Journal of Medicinal Chemistry; 2006; pp. 1006-1015; vol. 49, No. 3.

Virginie Lacronique, et al.; A TEL-JAK2 Fusion Protein with Constitutive Kinase Activity in Human Leukemia; Science; Nov. 14, 1997; pp. 1309-1312; vol. 278.

GenBank accession No. NM_019063; Source: http://www.ncbi.nlm.nih.gov/entrez/viewerfcgi?db=nuccore&id=19923496.

GenBank accession No. AB209477; Source: http://www.ncbi.nlm.nih.gov/entrez/viewerfcgi?db=nuccore&id=62088533.

Toshinori Iwahara, et al. "Molecular Characterization of ALK, a Receptor Tyrosine Kinase Expressed Specifically in the Nervous System"; Oncogene; Jan. 30, 1997; pp. 439-449; vol. 14; Stockton Press.

Luis Hernandez, et al.; "Diversity of Genomic Breakpoints in *TFG-ALK* Translocations in Anaplastic Large Cell Lymphomas"; American Journal of Pathology; Apr. 2002; pp. 1487-1494; vol. 160, No. 4.

Brandon Lawrence, et al.; "*TPM3-ALK* and *TPM4-ALK* Oncogenes in Inflammatory Myofibroblastic Tumors"; American Journal of Pathology; Aug. 2000; pp. 377-384; vol. 157, No. 2.

Martin U. Kuefer, et al.; Retrovirus-Mediated Gene Transfer of *NPM-ALK* Causes Lymphoid Malignancy in Mice; Blood; Oct. 15, 1997; pp. 2901-2910; vol. 90, No. 8.

Gisele W. B. Colleoni, et al.; "*ATIC-ALK*: A Novel Variant *ALK* Gene Fusion in Anaplastic Large Cell Lymphoma Resulting From the Recurrent Cryptic Chromosomal Inversion, inv(2)(p23q35)"; American Journal of Pathology; Mar. 2000; pp. 781-789; vol. 156, No. 3.

Tong Zhu, et al.; Polymer-Supported Synthesis of Pyridone-Focused Libraries as Inhibitors of Anaplastic Lymphoma Kinase; Journal of Combinatorial Chemistry; 2006; pp. 401-409; vol. 8, No. 3.

Kojo S.J. Elenitoba-Johnson, et al.; "Proteomic Identification of Oncogenic Chromosomal Translocation Partners Encoding Chimeric Anaplastic Lymphoma Kinase Fusion Proteins"; PNAS; May 9, 2006; pp. 7402-7407; vol. 103, No. 19.

Anna V. Galkin, et al.; "Identification of NVP-TAE684, a Potent, Selective, and Efficacious Inhibitor of *NPM-ALK*"; PNAS; Jan. 2, 2007; Epub2006 Dec, pp. 270-275; vol. 104, No. 1.

Manabu Soda, et al.; "Retroviral Expression Screening of Oncogenes in Primary Non-small-cell Lung Cancer"; O-324; Proceedings of the 65th Annual Meeting of the Japanese Cancer Association; Issued Aug. 28, 2006.

Manabu Soda, et al.; "Retroviral Expression Screening of Oncogenes in Primary Non-small-cell Lung Cancer"; O-324; Proceedings of the 65th Annual Meeting of the Japanese Cancer Association; Issued Aug. 28, 2006.

Hiroyuki Mano; "A Novel Transforming Fusion Kinase in Lung Cancer"; ML10 Proceedings of the 66th Annual Meeting of the Japanese Cancer Association; Issued Aug. 25, 2007.

K. Pulford, et al.; "The Emerging Normal and Disease-related Roles of Anaplastic Lymphoma Kinase"; Cellular and Molecular Life Sciences; 2004; pp. 2939-2953; vol. 61.

Klarisa Rikova, et al.; "Global Survey of Phosphotyrosine Signaling Identifies Oncogenic Kinases in Lung Cancer"; Cell; Dec. 14, 2007; pp. 1190-1203; vol. 131.

Ultan Mcdermott, et al.; "Identification of Genotype-correlated Sensitivity to Selective Kinase Inhibitors by Using High-throughput Tumor Cell Line Profiling"; PNAS; Dec. 11, 2007; pp. 19936-19941; vol. 104, No. 50.

Jussi P. Koivunen, et al.; "EML4-ALK Fusion Gene and Sensitivity to an ALK Kinase Inhibitor in Lung Cancer"; Proceedings of the American Association for Cancer Research Annual Meeting; #2373; Apr. 2008; vol. 49.

EML4-ALK FUSION GENE

BACKGROUND OF THE INVENTION

1. Field of the Invention

The present invention relates to a polypeptide as a novel fusion protein, a polynucleotide encoding the polypeptide, a vector comprising the polynucleotide, a transformed cell comprising the vector, and a therapeutic agent for cancer.

2. Background Art

Several cancer-related genes have been known so far. In particular, tyrosine kinase genes, which encode important enzymes directly regulating cell growth, have been known to be activated even by substitution or deletion in amino acid sequences and thereby bring about carcinogenesis.

For example, NPM-ALK fusion genes encoding NPM fused with ALK tyrosine kinase are observed in more than half of the cases of anaplastic large-cell lymphoma (ALCL) and the activation of ALK kinase has been shown to be important for tumor cell growth by NPM-ALK ("Science", (US), 1997, Vol. 278, p. 1309-1312, and "Science", (US), 1994, Vol. 263, p. 1281-1284).

The presence of a new type of abnormal kinase has been reported to be found in approximately 10% of lung cancer cases, and this report, however, has made no reference to specific molecules (Proceedings of the 65th Annual Meeting of the Japanese Cancer Association, O-324 (issued on Aug. 28, 2006)).

The echinoderm microtubule-associated protein like protein (EML4) (GenBank accession Number: NM_019063) has a basic region at the amino terminus, and further has carboxyl-terminal WD domains ("Genomics", (US), 2000, Vol. 68, p. 348-350). The physiological functions of EML4 have been little known.

On the other hand, Anaplastic Lymphoma Kinase (ALK) (GenBank accession Number: AB209477) is receptor tyrosine kinase (Oncogene. Jan. 30, 1997; 14 (4): 439-49). The ALK has a transmembrane domain in the middle, the carboxyl-terminal tyrosine kinase domain and amino terminal outer membrane domain(Oncogene. Jan. 30, 1997; 14 (4): 439-49).

Full-length ALK expression has been reported so far in some cancer cells of ectodermal origin, such as neuroblastoma, glioblastoma, breast cancer, and melanoma (the full-length ALK expression has not been observed in cancer cells of endodermal and mesodermal origins) ("International journal of cancer", (US), 2002, Vol. 100, p. 49-56). Full-length ALK is expressed in many neuroblastoma cell lines. However, the autophosphorylation of ALK is not observed in these neuroblastoma cell lines. Moreover, ALK expression has been reported, from the cohort analysis of neuroblastoma patients, to be weakly associated with cancer. It has been suggested that ALK expression in neuroblastoma may reflect its expression in normal neural differentiation, rather than its association with cancer ("Cellular and molecular life sciences", (Switzerland), 2004, Vol. 61, p. 2939-2953). On the other hand, in reported cases, ligands such as pleiotrophin and midkine as well as the gene amplification of ALK itself increase the autophosphorylation of ALK and mobilize intracellular signals. It has also been reported that ALK may contribute to cancer cell growth ("Journal of cellular physiology", (US), 2004, Vol. 199, p. 330-358).

In some cases of human malignant lymphoma and inflammatory myofibroblastic tumor, the ALK gene has been reported to be fused with other genes (NPM, CLTCL, TFG, CARS, SEC31L1, etc.) as a result of chromosomal translocation or inversion and thereby form a fusion type of tyrosine kinase ("Oncogene 9": 1567-1574, 1994, "Am J Pathol" 160: 1487-1494, 2002, "Science", (US), 1994, Vol. 263, p. 1281-1284, "Blood", (US), 1995, Vol. 86, p. 1954-1960, "Blood", (US), 2000, Vol. 95, p. 3204-3207, "Blood", (US), 1999, Vol. 94, p. 3265-3268, "Laboratory investigation; a journal of technical methods and pathology", (US), 2003, Vol. 83, p. 1255-1265, "International journal of cancer", (US), 2006, Vol. 118, p. 1181-1186, "Am J Pathol" 157: 377-384, 2000, "Blood" 90: 2901-2910, 1997, "Am J Pathol". 2000 Mar; 156 (3): 781-9). Moreover, a method for identifying a protein as a fusion partner for ALK using ALK antibodies has been reported ("PNAS" 2006 103, 7402-7407). On the other hand, a fusion gene of EML4 and ALK has not been reported. Since most partner molecules have a complex formation domain, the fusion protein itself has been thought to form a complex. This complex formation has been considered to cause loss of control of the tyrosine kinase activity of ALK and induce carcinogenesis with abnormally activated intracellular signals ("Cellular and molecular life sciences", (Switzerland), 2004, Vol. 61, p. 2939-2953). Indeed, it has been reported that the use of ALK shRNA or ALK kinase-inhibiting compound for lymphoma cells expressing ALK fusion proteins can induce cell growth inhibition and cell death. ALK inhibitor have been reported to inhibit lymphoma (PNAS, Jan, 2, 2007, 104 (1), 270-275 Epub2006 Dec). Therefore, it has been suggested that the ALK fusion protein may serve as a therapeutic target for lymphoma and inflammatory myofibroblastic tumor ("Blood", (US), 2006, Vol. 107, p. 689-697, "Blood", (US), 2006, Vol. 107, p. 1617-1623, "Laboratory investigation; a journal of technical methods and pathology", (US), 2005, Vol. 85, p. 1544-1554). It has also been suggested that ALK may serve as a therapeutic target for other cancers whose growth involves ALK as described above ("Blood", (US), 2006, Vol. 107, p. 1617-1623, "Laboratory investigation; a journal of technical methods and pathology", (US), 2005, Vol. 85, p. 1544-1554).

It has been reported that WHI-P131 and WHI-P154, which have been utilized as JAK3 tyrosine kinase-inhibiting substances, inhibit the activity of NPM-ALK ("Laboratory investigation; a journal of technical methods and pathology", (US), 2005, Vol. 85, p. 1544-1554). It has also been reported that low-molecular-weight ALK inhibitor induces the cell death of NPM-ALK-expressing lymphoma cell lines ("Blood", (US), 2006, Vol. 107, p. 1617-1623). In addition, plural low-molecular-weight compounds having an inhibitory activity against ALK have been reported so far ("Journal of medicinal chemistry", (US), 2006, Vol. 49, p. 1006-1015, "J Comb Chem." 8: 401-409, 2006, WO 2004/080980, WO 2005/009389, WO 2005/016894).

SUMMARY OF THE INVENTION

The present inventors successfully isolated, from samples obtained from lung cancer patients, the cDNA and genomic DNA of a novel fusion polynucleotide of a partial EML4 gene fused with a partial ALK gene as kinase. Analysis using clinical samples showed that the fusion polynucleotide is present in some lung cancer patients (Example 1). On the other hand, since the fusion polynucleotide is an oncogene that exhibits tumorigenicity (Example 2), it was revealed that the fusion polypeptide which is encoded by said fusion polynucleotide is a tool for screening a therapeutic agent for cancer that is shown to be positive for the fusion polynucleotide. Based on these findings, the present inventors constructed a method for screening an inhibitor of the fusion polynucleotide and/or the fusion polypeptide (i.e., a therapeutic agent for cancer that is shown to be positive for the fusion polynucleotide) causative of cancer, and confirmed that compounds obtained by screening exhibited an antitumor effect (Examples 5, 8 and 9). As a result, a test subject from which the fusion polynucleotide has been detected can receive cancer treatment using the inhibitor of the fusion polynucleotide and/or the polypeptide encoded thereby. According to a method for detecting the fusion polynucleotide or fusion protein in a sample obtained from a test subject, subjects to which the therapeutic agent is applicable can be selected. As a result, tailor-made medical care expected as highly effective treatment using the inhibitor can be carried out.

Based on these findings, the present inventors provided a novel polynucleotide and polypeptide useful as screening tools, and a method for treating cancer that is shown to be positive for the fusion gene of EML4 gene and ALK gene.

Specifically, the present invention relates to:

[1] An isolated polypeptide comprising the amino acid sequence of SEQ ID NO: 1 or the amino acid sequence with 95% or higher identity to the amino acid sequence of SEQ ID NO: 1 and having a kinase activity;

[2] The isolated polypeptide according to [1] consisting of the amino acid sequence of SEQ ID NO: 1;

[3] An isolated polynucleotide encoding the polypeptide according to [1];

[4] An expression vector comprising the polynucleotide according to [3];

[5] A cell transformed with the expression vector according to [4];

[6] A method for producing the polypeptide according to [1], comprising culturing a transformed cell according to [5] under conditions suitable for polypeptide expression and collecting the polypeptide from the cell;

[7] A method for treating cancer that is shown to be positive for a fusion gene of EML4 gene and ALK gene, comprising administering an effective amount of a substance inhibiting the polypeptide according to [1] to a target in need of treatment of cancer that is shown to be positive for a fusion gene of EML4 gene and ALK gene ; and

[8] The method for treating cancer that is shown to be positive for a fusion gene of EML4 gene and ALK gene according to [5], wherein the substance inhibiting the polypeptide according to any of claim 1 is 5-chloro-$N^4$-[2-(isopropylsulfonyl)phenyl]-$N^2$-{2-methoxy-4-[4-(4-methylpiperazin-1-yl)piperidin-1-yl]phenyl}pyrimidine-2,4-diamine or 2-[(5-bromo-2-{[2-methoxy-4-(4-methylpiperazin-1-yl)phenyl]amino}pyrimidin-4-yl)amino]-N-methylbenzenesulfonamide.

None of above-mentioned documents have reported the formation of a fusion gene by EML4 gene and ALK gene, let alone the expression of the fusion gene of EML4 gene and ALK gene in some cancer patients. The formation of a new type fusion gene by EML4 gene and ALK gene and the expression of this fusion gene in some cancer patients were found for the first time by the present inventors. EML4-ALK variant 1 and variant 2 and those transforming activity have been reported by inventor of the application (Nature 448, 561-566, 2 Aug. 2007 (online on 11 Jul. 2007)). Further, in the Nature article, it has been described that the fusion kinase is a promising candidate for therapeutic target as well as for a diagnostic molecular marker in non-small-cell lung cancer. However, above Nature article is the literature published within one year prior to the date of the present application. It has totally been unknown that known ALK inhibitors have therapeutic applications for cancer (particularly, lung cancer) that is shown to be positive for a fusion gene of EML4 gene and ALK gene. The method for treating cancer (particularly, lung cancer) that is shown to be positive for a fusion gene of EML4 gene and ALK gene is an invention that was provided for the first time by the findings of the present inventors.

The polypeptide, polynucleotide, expression vector, and cell of the present invention can be used in the screening of a substance inhibiting the polypeptide of the present invention (particularly, a therapeutic agent for lung cancer that is shown to be positive for a fusion gene of EML4 gene and ALK gene). Subjects for which a fusion gene of EML4 gene and ALK gene is positive (particularly, lung cancer patients) can be detected by using the presence of the polypeptide and/or polynucleotide of the present invention as an index. The substance inhibiting the polypeptide of the present invention is useful as a therapeutic agent for cancer, particularly lung cancer, that is shown to be positive for a fusion gene of EML4 gene and ALK gene.

DETAILED DESCRIPTION OF THE PREFERRED EMBODIMENTS

Hereinafter, the present invention will be described in detail. Gene manipulation techniques described herein can be practiced according to techniques known in the art, such as "Molecular Cloning", Sambrook, J et al., Cold Spring Harbor Laboratory Press, 1989, unless otherwise specified. Protein manipulation techniques described herein can be practiced according to techniques known in the art, such as "Experimental Protocol on Proteins", Shujunsha Co. Ltd. 1997, unless otherwise specified.

The phrase "the polypeptide of the present invention is inhibited" described herein encompasses both the phrases "the expression of the polypeptide of the present invention is inhibited" and "the activity of the polypeptide of the present invention is inhibited". A "substance inhibiting the polypeptide of the present invention" encompasses both a "substance inhibiting the expression of the polypeptide of the present invention" and a "substance inhibiting the activity of the polypeptide of the present invention".

<Polypeptide, Polynucleotide, Expression Vector, Transformed Cell, and Methods for Producing Polypeptide of the Present Invention>

The polypeptide of the present invention encompasses:

(1) a polypeptide consisting of the amino acid sequence of SEQ ID NO: 1 (hereinafter, referred to as a EML4-ALK fusion polypeptide v3);

(2) a polypeptide comprising the amino acid sequence of SEQ ID NO: 1 and having a kinase activity (hereinafter, referred to as a "polypeptide comprising v3").

(3) a polypeptide comprising an amino acid sequence with 95% or higher identity to the amino acid sequence of SEQ ID NO: 1 and having a kinase activity (hereinafter, referred to as a "v3 homologous polypeptide").

Preferably, the "v3 homologous polypeptide" has an amino acid sequence with 98% or higher, more preferably 99% or higher identity thereto.

The "identity" described herein means a value Identity obtained by NEEDLE program (J Mol Biol 1970; 48: 443-453) search using parameters prepared as defaults. The parameters are as follows:

Gap penalty=10
Extend penalty=0.5
Matrix=EBLOSUM62

The phrase "having a kinase activity" means having an activity as an enzyme phosphorylating tyrosine. Whether a certain polypeptide "has a kinase activity" is confirmed by a method of Example 3. More preferably, "polypeptide comprising v3" and "v3 homologous polypeptide" have combined kinase activity and tumorigenicity. Whether a certain polypeptide "has a tumorigenicity" is confirmed by a method of Example 2.

Up to this point, the polypeptide of the present invention has been described. Hereinafter, EML4-ALK fusion polypeptide v3, the "polypeptide comprising v3" and the "v3 homologous polypeptide" are collectively referred to as a "polypeptide of the present invention".

The polypeptide of the present invention is, preferably, the "polypeptide comprising the amino acid sequence of SEQ ID NO: 1 and having a kinase activity", more preferably, the "polypeptide comprising the amino acid sequence of SEQ ID NO: 1 and having a kinase activity and tumorigenicity", most preferably, the EML4-ALK fusion polypeptide v3.

A polynucleotide encoding the polypeptide of the present invention (hereinafter, referred to as a "polynucleotide of the present invention") is a polynucleotide of a nucleotide sequence encoding the EML4-ALK fusion polypeptide v3, "polypeptide comprising v3" or "v3 homologous polypeptide". The polynucleotide of the present invention is, preferably, a polynucleotide consisting of a nucleotide sequence encoding the amino acid sequence of SEQ ID NO: 1, more preferably, a polynucleotide consisting of the nucleotide sequence of SEQ ID NO: 2.

A "fusion gene of EML4 gene and ALK gene" described herein refers to the polynucleotide of the present invention. A gene encoding the EML4-ALK fusion polypeptide v3 is referred to as an "EML4-ALK fusion polynucleotide v3".

The phrase "cancer that is shown to be positive for a fusion gene of EML4 gene and ALK gene" described herein means cancer positive for the polynucleotide of the present invention (i.e., the polynucleotide of the present invention is present) and, preferably, means cancer positive for the EML4-ALK fusion polynucleotide v3 (i.e., the EML4-ALK fusion polynucleotide v3-positive cancer) (i.e., the EML4-ALK fusion polynucleotide v3 is present).

Methods for producing the polynucleotide of the present invention include, but not particularly limited to, (1) a method using polymerase chain reaction (PCR), (2) a method using a standard genetic engineering approach (i.e., a method comprising selecting a transformed strain comprising desired amino acid sequence from strains transformed with a cDNA library), and (3) a chemical synthesis method. Each method can be practiced in the same way as in WO 01/34785. However, the "novel protein of the present invention" described therein can be interpreted as a protein consisting of the polypeptide of the present invention described herein, and the "gene of the present invention" described therein can be interpreted as the polynucleotide of the present invention described herein.

In the method using PCR, the polynucleotide of the present invention can be produced, for example, according to procedures described in 1) Production method of protein gene, a) First production method in "Embodiments of the Invention" of the patent document. mRNA is extracted from cells or tissues having the ability to produce the protein of the present invention, for example, from lung tissues derived from a human patient with lung cancer. Subsequently, this mRNA can be subjected to reverse transcriptase reaction in the presence of random primers or oligo dT primers to synthesize single-stranded cDNA. The obtained single-stranded cDNA can be subjected to PCR using 2 primers interposing a partial region of the gene of interest to obtain the polynucleotide of the present invention or a portion thereof. More specifically, the polynucleotide of the present invention can be produced, for example, by a method described in Example 1.

Alternatively, the polynucleotide of the present invention may be produced by artificially synthesizing the polynucleotide of the present invention as separated fragments by reverse transcription (RT)-PCR and then fusing these obtained fragments.

The expression vector of the present invention, transformed cell of the present invention, and method for producing polypeptide of the present invention can be practiced, for example, according to procedures described in 2) Methods for the production of the vector of the invention, the host cell of the invention and the recombinant protein of the invention in "Mode for Carrying Out the Invention" of WO 01/34785. The isolated polynucleotide of the present invention can be incorporated again into appropriate vector DNA to thereby transform a eukaryotic or prokaryotic host cell therewith. Alternatively, an appropriate promoter and a sequence involved in phenotypic expression may be introduced to the vector to thereby cause each host cell transformed therewith to express the polynucleotide.

The expression vector of the present invention is not particularly limited as long as it comprises the polynucleotide of the present invention and it expresses the polypeptide of the present invention. Examples thereof can include an expression vector obtained by inserting the polynucleotide of the present invention into an expression vector known in the art, which is appropriately selected according to a host cell used.

Likewise, the cell of the present invention is not particularly limited as long as it comprises the polynucleotide of the present invention as a result of nucleic acid transfer by transfection or infection with the expression vector of the present invention. For example, the cell of the present invention is a host cell comprising the polynucleotide of the present invention incorporated in the chromosome or is a cell comprising the expression vector comprising the polynucleotide of the present invention. The cell of the present invention is obtained, for example, by transfecting or infecting a desired cell with the expression vector of the present invention. For example, The cell of the present invention is obtained as described in Example 2 and 3.

The desired transformed cell thus obtained can be cultured according to a standard method. A protein consisting of the polypeptide of the present invention is produced by this culture. A medium used in the culture can be selected appropriately according to a host cell used from among a variety of routine media. For example, an RPMI1640 medium supplemented with serum components such as fetal bovine serum (FBS) is used for the BA/F3 cell.

The polypeptide of the present invention thus produced by the transformed cell can be separated and purified by a variety of separation operation techniques known in the art using the physical or biochemical properties of the polypeptide.

The polypeptide of the present invention can be fused in frame with a marker sequence and expressed to thereby achieve the confirmation of expression of the protein as well as the purification of the protein.

<Screening Method>

The polypeptide, polynucleotide, expression vector, and cell of the present invention can be used in the screening of a substance inhibiting the polypeptide of the present invention (particularly, a therapeutic agent for lung cancer that is shown to be positive for a fusion gene of EML4 gene and ALK gene). The screening method encompasses a method for screening a therapeutic agent for cancer (preferably, lung cancer) that is shown to be positive for the polynucleotide of the present invention.

It was revealed that the EML4-ALK fusion polynucleotide v3 is an oncogene (Example 2) and the presence of the EML4-ALK fusion polynucleotide was detected in some lung cancer patients (Example 1). Further it was revealed that the anchorage-independent cell growth was inhibited (i.e., an anti-cancer effect is exhibited) by inhibiting the activity and/or expression of the polypeptide of the present invention (Example 5, 8). It was shown that the substance inhibiting the polypeptide of the present invention (inhibiting the activity and/or expression of the polypeptide of the present invention) has a therapeutic effect on cancer. Specifically, the method for screening a substance inhibiting the polypeptide of the present invention (inhibiting the activity and/or expression of the polypeptide of the present invention) can be utilized as a method for screening a therapeutic agent for cancer (preferably, lung cancer) that is shown to be positive for the polynucleotide of the present invention.

The method for screening a substance inhibiting the polypeptide is not particularly limited as long as it comprises the following steps (i) to (iii):

(i) bringing test substances into contact with the polypeptide of the present invention or a cell expressing the polypeptide of the present invention;

(ii) analyzing whether the polypeptide is inhibited or not, and (iii) selecting a substance inhibiting the polypeptide.

Preferably, the substance inhibiting the polypeptide of the present invention can be screened by methods described in Examples 3, 4, 5, 7, 8 and 9.

The screening method encompasses the following methods (a), (b), or (c)

(a) In vitro screening method;

a method for screening a substance inhibiting the activity of the polypeptide of the present invention, comprising the steps of (1) bringing test substances into contact with the polypeptide of the present invention, (2) analyzing whether the activity of the polypeptide is inhibited or not, and (3) selecting a substance inhibiting the activity of the polypeptide;

(b) Cell-based screening method;

a method for screening a substance inhibiting the activity of the polypeptide of the present invention, comprising the steps of (1) bringing test substances into contact with a cell expressing the polypeptide of the present invention, (2) analyzing whether the activity of the polypeptide is inhibited or not, and (3) selecting a substance inhibiting the activity of the polypeptide; and (c) Expression inhibition-based screening method;

a method for screening a substance inhibiting the expression of the polypeptide of the present invention, comprising the steps of (1) bringing test substances into contact with a cell expressing the polypeptide of the present invention, (2) analyzing whether the expression of the polypeptide is inhibited or not, and (3) selecting a substance inhibiting the expression of the polypeptide.

Each screening method (a)-(c) will be described below. The cell expressing the polypeptide of the present invention comprises a cell naturally expressing the polypeptide of the present invention (e.g., NCI-H2228) and a cell caused to express the polypeptide of the present invention by its transformation with a vector comprising the polynucleotide of the present invention. Preferable cell is the cell caused to express the polypeptide of the present invention by its transformation with a vector comprising the polynucleotide of the present invention.

(a) In Vitro Screening Method

The in vitro screening method comprises: bringing test substances into contact with the purified polypeptide of the present invention by addition (contact step); analyzing whether the activity of the polypeptide of the present invention is inhibited or not by the test substance(s), by comparison with the activity of the polypeptide of the present invention not brought into contact with the test substances (analysis step); and selecting a substance inhibiting the activity of the polypeptide of the present invention (i.e., a therapeutic agent for cancer, particularly, a therapeutic agent for lung cancer).

In the screening method of the specification, each step can specifically be practiced, for example, as described below. Test substances are brought into contact with the purified polypeptide of the present invention by addition. After the addition of ATP, the activity of the polypeptide is measured. Solvents (e.g., DMSO) for the test substances are brought as a control into contact with the purified polypeptide by mixing. After the addition of ATP, the activity of the polypeptide is measured. A condition without the addition of ATP can be set as a background control. Whether the activity of the polypeptide of the present invention is inhibited or not by the test substance(s) is analyzed. Whether the activity (i.e., phosphorylating activity) of the polypeptide of the present invention is inhibited or not by the test substance(s) can be determined by analyzing a test substance-induced change in the tyrosine phosphorylation level of the polypeptide of the present invention. Specifically, when the addition (i.e., contact) of a test substance inhibits the activity (i.e., phosphorylating activity) of the polypeptide of the present invention as compared with the addition (i.e., contact) of the solvent control, this test substance is selected as a substance inhibiting the activity of the polypeptide of the present invention (i.e., a therapeutic agent for cancer, particularly, a therapeutic agent for lung cancer). In vitro screening method of the specification comprises a screening method carried out in a manner similar as above except in the above steps, the peptide substrate is added and mixed before the addition of ATP, and activity of the polypeptide of present invention is determined by analyzing phosphorylation activity on the peptide substrate by the polypeptide of the present invention ( i.e., analyzing a change in the phosphorylation level on the peptide substrate by the polypeptide of the present invention in order to determine whether a test substance inhibits the activity of the polypeptide of the present invention). Of the screening methods of the specification, preferably, the in vitro screening method is practiced under the conditions described in Example 3. A substance that can inhibit 50% or more activity by this method at a concentration of 10 µM or lower, preferably 1 µM or lower, more preferably 0.1 µM or lower is selected as a substance inhibiting the activity of the polypeptide of the present invention.

(b) Cell-based Screening Method

The cell-based screening method comprises: bringing test substances into contact with a cell expressing the polypeptide of the present invention by mixing (i.e., addition) (contact step); analyzing whether the activity of the polypeptide of the present invention is inhibited or not by the test substance(s), by comparison with the activity of the polypeptide of the present invention not brought into contact with the test substances (analysis step); and selecting a substance inhibiting the activity of the polypeptide of the present invention (i.e., a therapeutic agent for cancer, particularly, a therapeutic agent for lung cancer). This screening method can specifically be practiced, for example, as described below.

First, test substances or solvent controls (e.g., DMSO) are brought into contact with a cell expressing the polypeptide of the present invention. The cells are cultured for a given time. The activity (i.e., autophosphorylating activity) of the polypeptide of the present invention is measured using cell lysates prepared from the cultured cells by dissolution, by SDS electrophoresis known in the art and immunoblotting using an anti-phosphorylated ALK antibody (e.g., Cell Signaling Technology) to thereby analyze whether the activity of the polypeptide of the present invention is inhibited or not by the test substance(s). Whether the activity of the polypeptide of the present invention is inhibited or not by the test substance(s) can be determined by analyzing a test substance-induced change in the tyrosine phosphorylation (i.e., autophosphorylation) level of the polypeptide of the present invention. Specifically, when the addition (i.e., contact) of a test substance inhibits the activity of the polypeptide of the present invention as compared with the addition (i.e., contact) of the solvent control, this test substance is selected as a substance inhibiting the activity of the polypeptide of the present invention (i.e., a therapeutic agent for cancer, particularly, a therapeutic agent for lung cancer). Of the screening methods of the present specification, preferably, the cell-based screening method is practiced under the conditions described in Example 4 and 7. A substance that can inhibit 50% or more activity by this method at a concentration of 10 µM or lower, preferably 1 µM or lower, more preferably 0.1 µM or lower is selected.

(c) Expression Inhibition-based Screening Method

The expression inhibition-based screening method comprises: bringing test substances into contact with a cell expressing the polypeptide of the present invention by mixing (i.e., addition) (contact step); analyzing whether the expression of the polypeptide of the present invention is inhibited or not by the test substance(s), by comparison with the expression of the polypeptide of the present invention not brought into contact with the test substances (analysis step); and selecting a substance inhibiting the expression of the polypeptide of the present invention (i.e., a therapeutic agent for cancer, particularly, a therapeutic agent for lung cancer, that is shown to be positive for the polynucleotide of the present invention). This screening method can specifically be practiced, for example, as described below.

Test substances or solvent controls (e.g., DMSO) are brought into contact with any cell expressing the polypeptide of the present invention. After culture, extracts are prepared from the cells and subsequently used to analyze whether the expression of the polypeptide of the present invention is inhibited or not by the test substance(s). Whether the expression of the polypeptide of the present invention is inhibited or not can be analyzed by analyzing whether the mRNA or protein expression of the polypeptide of the present invention is inhibited or not. More specifically, the mRNA or protein level of the polypeptide of the present invention present in the cell extracts is identified by an expression level analysis method known in the art, for example, northern blotting, quantitative PCR, immunoblotting, or ELISA. Whether the expression of the polypeptide of the present invention is inhibited or not by the test substance(s) can be determined by analyzing a test substance-induced change in the expression level of the polypeptide of the present invention. Specifically, when the contact of a test substance inhibits the expression level (i.e., mRNA or protein level) of the polypeptide of the present invention as compared with the contact of the solvent control, this test substance is selected as a substance inhibiting the expression of the polypeptide of the present invention (i.e., a therapeutic agent for cancer, particularly, a therapeutic agent for lung cancer). A substance that can inhibit 50% or more activity by this method at a concentration of 10 µM or lower, preferably 1 µM or lower, more preferably 0.1 µM or lower is selected. Preferably, the selected test substance has an inhibitory activity on all cells used. However, a test substance having an inhibitory activity on one cell can also be selected.

The screening method of the present specification further comprises, in addition to analyzing whether the polypeptide of the present invention is inhibited or not and selecting a substance inhibiting the polypeptide of the present invention, the step of confirming that the selected test substance has a therapeutic activity against cancer (particularly, lung cancer) that is shown to be positive for the polynucleotide of the present invention.

The Step of Confirming that the Selected Test Substance has a Therapeutic Activity Against Cancer Examples of the step of confirming that the selected substance has a therapeutic activity against cancer (particularly, lung cancer) that is shown to be positive for the polynucleotide of the present invention include a step of practicing an evaluation method known in the art or a modified method thereof, for example, a method comprising analyzing the therapeutic activity of the selected substance against cancer (particularly, lung cancer) by treating, with the substance, cultured cells or tumor model animals expressing the polypeptide of the present invention (Clinical Oncology, 2nd ed., Cancer and Chemotherapy Publishers, Inc.).

The step of confirming that the selected test substance has a therapeutic activity against cancer (particularly, lung cancer) that is shown to be positive for the polynucleotide of the present invention is, preferably, the step of confirming that the selected test substance exhibits the growth-inhibiting effect and/or cell death-inducing effect on the cells using human cancer-derived (particularly, lung cancer-derived) cancer cells endogenously expressing the polypeptide of the present invention (e.g., NCI-H2228), the step of confirming that the selected test substance has the inhibitory effect on the anchorage-independent growth of cells transformed by the expression of the polypeptide of the present invention, and/or the step of confirming that the selected test substance has the inhibitory effect on the growth of tumor formed in immunodeficient mouse inoculated with a cell expressing the polynucleotide of the present invention.

A cancer-bearing model animal serving as a tumor model animal can be used in which the cancer cells endogenously expressing the polypeptide of the present invention (e.g., NCI-H2228) or the cells transformed by the expression of the polypeptide of the present invention are transplanted subcutaneously, intradermally, intravenously or intraperitoneally or into each organ (e.g., a nude mouse in which NIH3T3 cells caused to express the polypeptide of the present invention are transplanted). Furthermore, an animal caused to overexpress the EML4-ALK fusion polynucleotide can also be used.

Preferably, a therapeutic agent for lung cancer that is shown to be positive for the polypeptide of the present invention can be screened by methods described in Examples 5, 8 and 9.

Examples of the test substances used in the screening method of the present invention can include, but not particularly limited to, commercially available compounds (including peptides), a variety of compounds (including peptides) known in the art and registered in chemical files, compound groups obtained by a combinatorial chemistry technique (N. Terrett et al., Drug Discov. Today, 4 (1): 41, 1999), microorganism culture supernatants, plant- or marine organism-derived natural components, animal tissue extracts, double-stranded nucleic acids, antibodies or antibody fragments, and compounds (including peptides) chemically or biologically modified from compounds (including peptides) selected by the screening method of the present invention.

<Method for Treating Cancer that is Shown to be Positive for the Polynucleotide of the Present Invention>

The present invention encompasses method for treating cancer that is shown to be positive for the polynucleotide of the present invention, comprising administering an effective amount of a substance inhibiting the polypeptide of the present invention (e.g., a substance obtained by the screening method of the present specification [e.g., a double-stranded nucleic acid (including siRNA), protein (including an antibody or antibody fragment), peptide, or other compounds]) to a subject in need of treatment of cancer that is shown to be positive for the polynucleotide of the present invention.

As a substance in the method for treating cancer that is shown to be positive for the polynucleotide of the present invention, the following pharmaceutical composition (hereinafter, referred to as pharmaceutical composition of the present specification) can be used. The active ingredient in the pharmaceutical composition can be selected by the screening method of the present specification. Examples of the substance selected by the screening method of the present specification can include compounds A to D. Alternatively, a compound selected by the screening method of the present specification from a low-molecular-weight compound with an inhibitory activity against ALK (ALK inhibitor) known in the art can be used as an active ingredient in the pharmaceutical composition. The ALK inhibitor can be exemplified by ALK inhibitors described in WO 2005/097765 and WO 2005/016894 (particularly, 2,4-pyrimidinediamine derivatives). Particularly, a compound described in Wan W et al., Blood 107: 1617-1623, 2006 as well as WHI-P131 (4-(4'-Hydroxyphenyl)amino-6,7-dimethoxyquinazoline) and WHI-P154 (4-[(3'-Bromo-4'-hydroxyphenyl)amino]-6,7-dimethoxyquinazoline; hereinafter, referred to as a compound A); ) (both, EMD Biosciences; Marzec M et al., Lab Invest 85: 1544-1554, 2005) can be used. Alternatively, N-[2-(3-chlorophenyl)ethyl]-2-[({[4-(trifluoromethoxy)phenoxy] acetyl}amino)methyl]-1,3-thiazole-4-carboxamide (WO 2005/097765; hereinafter, referred to as a compound B), 5-chloro-$N^4$-[2-(isopropylsulfonyl)phenyl]-$N^2$-{2-methoxy-4-[4-(4-methylpiperazin-1-yl)piperidin-1-yl] phenyl}pyrimidine-2,4-diamine (WO 2005/016894; hereinafter, referred to as a compound C), or 2-[(5-bromo-2-{[2-methoxy-4-(4-methylpiperazin-1-yl)phenyl] amino}pyrimidin-4-yl)amino]-N-methylbenzenesulfonamide (WO 2005/016894; hereinafter, referred to as a compound D) can be used as an ALK inhibitor.

The double-stranded nucleic acid exemplified as an active ingredient in the pharmaceutical composition comprises a double-stranded nucleic acid (RNA or DNA) portion and, preferably, 3'-terminal overhangs of the sense and antisense strands and induces RNAi. The RNAi is an evolutionarily conserved phenomenon, which occurs via a double-stranded nucleic acid with 21 to 23 bases produced by RNase III endonuclease (Genes Dev. 15, 485-490, 2001). The 3'-terminal overhangs are respectively any nucleic acid with 1 or 2 bases, preferably 2 bases. The number of bases (21 to 23 bases) described above is the number of bases of the sense or antisense strand including its overhang. The sense and antisense strands can have the same number of bases or a different number of bases and, preferably, have the same number of bases.

For example, U (uridine), A (adenosine), G (guanosine), or C (cytidine) can be used as ribonucleic acids constituting the 3'-terminal overhangs of the double-stranded nucleic acid. For example, dT (deoxythymidine), dA (deoxyadenosine), dG (deoxyguanosine), or dC (deoxycytidine) can be used as deoxyribonucleic acids constituting the 3'-terminal overhangs thereof The double-stranded nucleic acid can be produced by standard methods (e.g., J. Am. Chem. Soc., 120, 11820-11821, 1998; and Methods, 23, 206-217, 2001). Alternatively, a contract manufacturer for double-stranded nucleic acids (e.g., RNAi Co., Ltd.) is well known by those skilled in the art and can be utilized in the production of the double-stranded nucleic acid.

A therapeutic effect on cancer that is shown to be positive for the polynucleotide of the present invention can be confirmed by use of a method generally known by those skilled in the art or a modified method thereof (see "The step of confirming that the selected test substance has a therapeutic activity against cancer").

A preparation comprising, as an active ingredient, a substance inhibiting the polypeptide of the present invention (e.g., a substance [e.g., a double-stranded nucleic acid, protein (including an antibody or antibody fragment), peptide, or other compounds] obtained by the screening method of the present specification) can be prepared as a pharmaceutical composition using pharmacologically acceptable carriers, excipients, and/or other additives usually used in the preparation production according to the type of the active ingredient.

Examples of administration can include: oral administration using tablets, pills, capsules, granules, subtle granules, powders, or oral liquid agents; and parenteral administration using injections for intravenous injection (including intravenous drip), intramuscular injections, or subcutaneous injection, suppositories, percutaneous administration agents, or transmucosal administration agent. Particularly, parenteral administration such as intravenous injection is preferable for peptides that are digested in the stomach.

To prepare a solid composition for oral administration, 1 or more active substances can be mixed with at least one inactive diluent, for example, lactose, mannitol, glucose, microcrystalline cellulose, hydroxypropylcellulose, starch, polyvinyl pyrrolidone, or magnesium aluminometasilicate. The composition can contain additives other than the inactive diluent, for example, lubricants, disintegrants, stabilizers, or solvents or solubilizers according to a standard method. Tablets or pills can be coated, if necessary, with a sugar coating or with a film such as a gastrosoluble or enteric substance.

A liquid composition for oral administration can comprise, for example, an emulsion, solution, suspension, syrup, or elixir and can contain an inactive diluent generally used, for example, purified water or ethanol. The composition can contain additives other than the inactive diluent, for example, moisturizers, suspensions, sweeteners, flavors, or antiseptics.

A parenteral injection can comprise an aseptic aqueous or non-aqueous solution, suspension, or emulsion. A water-soluble solution or suspension can contain, for example, distilled water or saline for injection, as a diluent. A water-insoluble solution or suspension can contain, for example, propylene glycol, polyethylene glycol, plant oil (e.g., olive oil), alcohols (e.g., ethanol), or polysorbate 80 as a diluent. The composition can further contain moisturizers, emulsifiers, dispersants, stabilizers, solvents or solubilizers, or antiseptics. The composition can be sterilized, for example, by filtration using a bacterium-impermeable filter, formulation of germicides thereinto, or irradiation. Alternatively, an aseptic solid composition can be produced and dissolved in aseptic water or other aseptic media for injection for use.

A dose can be determined appropriately in consideration of the activity intensity of the active ingredient, that is, the substance obtained by the screening method of the present specification, conditions, the age or gender of a subject receiving administration, and so on. Preferably, the dose can be calculated according to a route as an amount that gives a serum concentration around tumor or intratumoral concentration 3 to 30 timers, for example, 10 times, higher than a drug concentration inhibiting 50% of the activity or expression of the polypeptide of the present invention. For example, the dose in oral administration in adult (60 kg in body weight) is usually approximately 0.1 to 100 mg/day, preferably, 0.1 to 50 mg/day. The dose in parenteral administration is 0.01 to 50 mg/day, preferably, 0.01 to 10 mg/day, in terms of an injection.

A therapeutic target by the pharmaceutical composition is a test subject from which the presence of the polynucleotide of the present invention and/or the polypeptide of the present invention has been detected. The substance inhibiting the polypeptide of the present invention kills cells that have transformed due to the EML4-ALK fusion polynucleotide v3. Therefore, the substance inhibiting the polypeptide of the present invention serves as an effective therapeutic agent for cancer (particularly, lung cancer) that is shown to be positive for the polynucleotide of the present invention.

EXAMPLES

The present invention will be described in detail below by Examples, but the present inventions are not limited by these Examples. Further, unless otherwise stated the process of the present invention can be carried out according to publicly known methods. Also, commercially available reagents and kits can be used in accordance with the instructions of the commercial products.

Anti-phosphorylated ALK antibody and anti-ALK antibody used were produced by Cell Signaling Technology Inc. and NEOMARKERS Inc., respectively.

Example 1

Detecting EML4-ALK Fusion Polynucleotide v3 in Clinical Specimens and Cloning of EML4-ALK Fusion Polynucleotide v3

PCR (after 50° C. for 2 minutes and 95° C. for 15 minutes, 50 cycles of 94° C. for 15 seconds, 60° C. for 30 seconds and 72° C. for 90 seconds) was carried out using 75 cDNA prepared from the non-small cell lung cancer clinical specimens and a quantitative PCR kit (QuantiTect SYBR Green; Qiagen Inc.) and oligonucleotides of SEQ ID NOs: 3 and 4 as primers. As a result, in two cases, it was confirmed a sequence of 515 bp (SEQ ID NO:5) or 548 bp (SEQ ID NO:6) made by fusion of a part of EML4 and a part of ALK, which has a fusion point different from EML4-ALK variant 1 and EML4-ALK variant 2 (Nature 2007;448:561-566), was amplified.

Using the cDNA of a patient that is shown to be positive for PCR product described above as a template and oligonucleotides of SEQ ID NOs: 7 and 8 as primers, PCR (35 cycles of 98° C. for 10 seconds and 68° C. for 6 minutes) was carried out with a DNA polymerase (PrimeStar HS DNA polymerase, Takara Bio Inc.). The PCR product was cloned in pT7Blue-2 vector. As a result, new polynucleotide (SEQ ID NO: 2) which consisted of 700 bases from the start codon ATG of the EML4 gene to the portion of intron 6 and 1691 bases from the ALK gene exon 21 to the stop codon of the exon 30 was obtained. The plasmid in which the cDNA of SEQ ID NO: 2 was cloned was designated as EML4-ALKv3/pT7Blue-2.

Example 2

Investigation of Tumorgenicity of EML4-ALK Fusion Polypeptide v3

The EML4-ALK fusion polypeptide v3 expression vector (designated as EML4-ALKv3/pMXS) was constructed by subcloning the insert of the EML4-ALKv3/pT7Blue-2 in pMXS plasmid (JBC 275, 24945-24952, 2000). Also, using the EML4-ALKv3/pT7Blue-2, an expression vector (designated as FLAG-EML4-ALKv3/pMX-iresCD8) which expresses both EML4-ALK fusion polypeptide v3 having the FLAG tag at the N-terminus and CD8 was constructed by subcloning the insert in pMX-iresCD8 plasmid (JBC 276, 39012-39020, 2001). The 3T3 cells transfected with the EML4-ALKv3/pMXS described above were inoculated subcutaneously to nude mice at $5 \times 10^6$ cells/mouse and observed after 20 days. It turned out that tumor was formed. Because the EML4-ALK fusion polypeptide v3 was tumorgenic, it was indicated the polynucleotide of SEQ ID NO:2, which is one of the polynucleotides of the EML4-ALK fusion polynucleotide v3, is the causal gene of cancer. Hereinafter, the 3T3 cells in which EML4-ALK fusion polypeptide v3 is expressed are designated as the v3 expressing 3T3 cells.

Example 3

Method for Screening for the EML4-ALK Fusion Polypeptide v3 Inhibitors

A recombinant retrovirus was produced according to a method of previous report (BBRC 356, 723-726, 2007) using FLAG-EML4-ALKv3/pMX-iresCD8. Mouse lymphatic cell line BA/F3 cells were infected therewith. The EML4-ALK fusion polypeptide v3 expressing BA/F3 cells were cultured in RPM1640 medium containing 10% of fetal bovine serum. To prepare the EML4-ALK fusion polypeptide v3, about $2 \times 10^9$ cells were collected. After washing 3 times with PBS, cells were lysed in a lysis solution (50 mM Tris.HCl (pH7.4), 150 mM NaCl, 1% Triton X100, 5 mM EDTA, 5 mM EGTA, 1 mM NaVO$_4$, 1 mM DTT and protease inhibitor cocktail complete). The EML4-ALK fusion polypeptide v3 present in the supernatant obtained after a centrifugation was purified using ANTI-FLAG M2 Affinity Gel (SIGMA-ALDRICH Inc) according to the method described in the product information document. For washing and elution, the washing solution (50 mM Tris.HCl (pH7.4), 250 mM NaCl, 0.05% Brij35, 1 mM EDTA, 1 mM EGTA, 1 mM NaVO$_4$, 1 mM DTT, complete) and the elution solution (50 mM Tris.HCl (pH7.4), 150 mM NaCl, 0.05% Brij35, 1 mM DTT, 0.5 mg/mL FLAG peptide) were used, respectively. Immunoblotting using anti-ALK antibody and anti FLAG M2 antibody (SIGMA-ALDRICH Inc.) and silver staining were carried out for the eluate to detect the EML4-ALK fusion polypeptide v3. It was demonstrated that the EML4-ALK fusion polypeptide v3 can be prepared by this method.

The EML4-ALK fusion polypeptide v3 purified as described above was diluted in a reaction solution (15 mM Tris HCl (pH7.4), 0.25 mM MgCl$_2$, 0.01% Tween-20, 2 mM DTT), and then ATP was not added or ATP 20 µM was added. The respective mixtures were reacted at room temperature for 1 hour. After the reaction, the auto phosphorylated EML4-

ALK fusion polypeptide v3 and the EML4-ALK fusion polypeptide v3 were detected by immunoblotting using anti-phosphorylated ALK antibody, which recognizes specifically the product phosphorylated at the 1604th tyrosine residue of ALK, and anti-ALK antibody, and quantitated by an image analysis system (VersaDoc Imaging System; Bio-Rad Inc.). The amount of phosphorylation was calibrated by dividing the count of the autophosphorylated EML4-ALK fusion polypeptide v3 by the count of the EML4-ALK fusion polypeptide v3. As the result, the autophosphorylated EML4-ALK fusion polypeptide v3 band was detected at the location of about 90 kDa under the condition of ATP addition. In addition, the phosphorylation activity toward a peptide substrate was investigated using a kinase activity detection kit (HTRF KinEASE-TK; Cisbio Inc.). Using TK substrate 1, which was included in the kit, as the substrate, and after adding no ATP or 100 µM ATP, the mixtures were reacted at room temperature for 1 hour, and the count of HTRF was detected as recommended by the kits manufacturer. As the result it became clear that the count of HTRF (that is, phosphorylation of the peptide substrate) was increased by about 20 times by the addition of ATP compare to no addition of ATP. As shown above, the in vitro kinase activity of the EML4-ALK fusion polypeptide v3 can be detected using anti-phosphorylated ALK antibody and the kinase activity detection kit.

The inhibitory effect of compound A-D against the in vitro kinase activity of the EML4-ALK fusion polypeptide v3 was investigated using the method above. As the result, it was found that compound A-D inhibited the autophosphorylation and the phosphorylation activity on the peptide substrate by the purified EML4-ALK fusion polypeptide v3 (Table 1). These compounds could be selected as substances which inhibited the activity of the EML4-ALK fusion polypeptide v3.

TABLE 1

| Compound | Final concentration | Inhibition on autophosphorylation | Inhibition on peptide substrate |
|---|---|---|---|
| A | 10 µM | 100% | 98% |
| B | 10 µM | 100% | 77% |
| C | 10 nM | 103% | 100% |
| D | 10 nM | 107% | 98% |

The above results indicated that screening (an in vitro type screening) for a substance which inhibits the activity of the polypeptide of the present invention could be performed by preparing the EML4-ALK fusion polypeptide v3 and using the in vitro kinase activity as an index.

Example 4

Screening for the Substances which Inhibit an Intracellular Autophosphorylation Activity of the EML4-ALK Fusion Polypeptide v3

DMSO (control) or compound A-D were added to v3 expressing 3T3 cells (Example 2) at 10 µM or 10 nM for 4 hours and the amount of phosphorylation of tyrosine of EML4-ALK fusion polypeptide v3 and the total protein amount of the EML4-ALK fusion polypeptide v3 were measured and the inhibition rate of respective compounds on intracellular kinase activity was calculated in a similar manner as in Example 3.

Each compound clearly inhibited the kinase activity of the EML4-ALK fusion polypeptide v3 in the v3 expressing 3T3 cells (Table 2). It was confirmed that screening for the substances inhibiting the activity of the polypeptide of the present invention (cell-based screening) could? be performed using the EML4-ALK fusion polypeptide v3.

TABLE 2

| Compound | Final concentration | Inhibition on autophosphorylation (v3 expressing 3T3 cells) |
|---|---|---|
| A | 10 µM | 94% |
| B | 10 µM | 76% |
| C | 10 nM | 95% |
| D | 10 nM | 106% |

Example 5

Inhibitory Effect of the Inhibitors of EML4-ALK Fusion Polypeptide on Anchorage Independent Growth of the v3 Expressing 3T3 Cells Measurement for anchorage independent cell growth (colony method, etc) has been known to be a system for investigating an antitumor effect (pharmacologic effect) of compounds (Clinical Oncology, second edition, Cancer and Chemotherapy Publishers Inc.). In place of the colony method, there is a following method using spheroid plates for measuring the growth of non-attached cells.

The v3 expressing 3T3 cells (Example 2) were seeded to a 96 well spheroid plate (Sumilon Celltight Spheroid 96U, Sumitomo Bakelite Inc.) at 3000 cells per well in a medium (Invitrogen) containing 10% fetal bovine serum. Under 5% $CO_2$, cells were cultured overnight at 37° C., and then compound A or B was added to a final concentration of 10 µM, compound C or D was added to a final concentration of 30 nM and as a negative control the solvent of the compounds, DMSO, was added to make the same concentration as the compounds. At the same time, cells were counted before the addition of drugs (Day 0). Then, cells were cultured under 5% $CO_2$, at 37° C. for 3 days, mixed with a reagent for measuring cell number (CellTiter-Glo™ Luminescent Cell Viability Assay; Promega Inc.) stirred for 20 minutes, and the measurements (day 3) were carried out using a luminometer (ML3000 microtiter plate luminometer; Dynatech Laboratories Inc.). The results showed that all the compounds had growth inhibitory activity on v3 expressing 3T3 cells. The inhibition rate of the compounds was calculated assuming the cell number at Day 0 and Day 3 were 100% inhibition and 0% inhibition, respectively. The results showed that all the compounds had growth inhibitory activity on v3 expressing 3T3 cells (Table 3).

TABLE 3

| Compound | Final concentration | Inhibitory activity on v3 expressing 3T3 cells |
|---|---|---|
| A | 10 µM | 172% |
| B | 10 µM | 53% |
| C | 30 nM | 182% |
| D | 30 nM | 206% |

Above results indicate that compound A-D inhibited the anchorage independent cell growth of v3 expressing 3T3 cells by inhibiting the kinase activity of the EML4-ALK fusion polypeptide v3.

Example 6

The Expression and Cloning of v3 Homologous Polypeptide mRNA in NCI-H2228 Cells Using the cDNA which prepared by reverse transcription from total RNA of NCI-H2228 cells, a human non-small cell lung cancer cell line (American Type Culture Collection) as a template, PCR (35 cycles of 98° C. for 10 seconds, 68° C. for 4 minute) was carried out using oligonucleotides of the SEQ ID NO: 7 and the SEQ ID NO: 8 as primers and a DNA polymerase (primeSTAR HS DNA polymerase, Takara Bio Inc.). Using a part of the PCR product as a template, PCR (35 cycles of 98° C. for 10 seconds, 68° C. for 4 minute) was carried out using an oligonucleotide of the SEQ ID NO:9 which was provided with the cleavage sequence of restriction enzyme HindIII at the 5' terminus side of the start codon ATG of the EML4 gene and an oligonucleotide of SEQ ID NO: 10 which was provided with the cleavage sequence of restriction enzyme Xba I at the 3' terminus side of stop codon TGA of ALK gene as primers and a DNA polymerase (Pyrobest DNA polymerase; Takara Bio Inc.). PCR product of about 2400 bp was obtained. This product was cloned into pCR2.1-TOPO vector using TOPO TA Cloning kit (Invitrogen Inc.), and DNA sequence was analyzed. As a result, two kinds of polynucleotide were identified. One was a 2391 bp sequence (SEQ ID NO:11) which was different in 4 bases, namely, 685th, 903rd, 2000th, and 2115th bases from SEQ ID NO:2 (Example 1). The polypeptide of SEQ ID NO:12 which is encoded by the polynucleotide of SEQ ID NO:11 is different from the polypeptide of SEQ ID NO:1 in 3 amino acids, namely, at 229th, 667th, and 705th amino acids of SEQ ID NO: 1. The another was a 2358 bp sequence (SEQ ID NO:13) which consisted of 667 bases from the start codon ATG of the EML4 gene to the exon 6 and 1691 bases from the ALK gene exon 21 to the stop codon of the exon 30. This sequence is different from SEQ ID NO:2 in that the sequence has 3 base substitutions (at the 903rd, 2000th, and 2115th bases of SEQ ID NO:2), and a deletion of 33 bases (from the 668th to the 700th base of SEQ ID NO:2). The polypeptide of SEQ ID NO:14, which is encoded by the polynucleotide of SEQ ID NO:13, is different from SEQ ID NO:1 in 2 amino acid substitutions (at the 667th and 705th amino acids of SEQ ID NO: 1) and in 11 amino acid deletions (from the 223rd to the 233rd amino acid of SEQ ID NO: 1). The polypeptide of SEQ ID NO: 14 shows 98.4% identities with the polypeptide of SEQ ID NO: 1. The portion corresponding to these ALK gene was different about 1 base from the sequence (4080-5770) of NM_004304 registered in Genbank, without the amino acid variation. Therefore, It was suggested that the differences in portion of ALK gene between the polynucleotide (SEQ ID NO:2) identified in lung cancer patients and the polynucleotide (SEQ ID NO:11) cloned from NCI-H2228 were the polymorphism. Neither the EML4-ALK variant 1 (Nature 2007;448:561-566) nor the EML4-ALK variant 2 (Nature 2007;448:561-566) endogenously expressed in NCI-H2228 cells.

Example 7

Screening for the Substances which Inhibit an Intracellular Autophosphorylation Activity of the v3 Homologous Polypeptide on NCI-H2228 Cells DMSO (control) or compound C was added to NCI-H2228 cells at 100 nM as a final concentration and the amount of phosphorylation of tyrosine of v3 homologous polypeptide and the inhibition rate of compound C on autophosphorylation activity was calculated in a similar manner as in Example 4. Compound C inhibited the kinase activity of the v3 homologous polypeptide in the NCI-H2228 cells at 81%. It was confirmed that screening for the substances inhibiting the activity of the EML4-ALK fusion polypeptide of the present invention (cell type screening) could be performed by using as an index the autophosphorylation in the NCI-H2228 cells.

Example 8

Inhibitory Effect of the Inhibitors of EML4-ALK Fusion Polypeptide v3 on Anchorage Independent Growth of NCI-H2228 Cells DMSO (control) or compound A-D was added to the NCI-H2228 cells at 10 µM or 30 nM and this investigation was performed by a similar manner described as in Example 5, except cells were cultured for 5 days after the addition of drugs. The results showed that the compound A-D had growth inhibitory activity on the NCI-H2228 cells. The inhibition rate of the compounds was calculated assuming the cell number at Day 0 and Day 5 were 100% inhibition and 0% inhibition, respectively (Table 4).

TABLE 4

| Compound | Final concentration | Inhibitory activity on NCI-H2228 cells |
| --- | --- | --- |
| A | 10 µM | 164% |
| B | 10 µM | 102% |
| C | 30 nM | 137% |
| D | 30 nM | 141% |

Above results indicate that compound A-D inhibited the anchorage independent cell growth of NCI-H2228, non-small cell lung cancer cells, by inhibiting the kinase activity of the v3 homologous polypeptide. From the above results, it became clear that inhibitor against the polypeptide of the present invention was useful as a therapeutic agent for the polynucleotide of the present invention positive lung cancer patients.

Example 9

Anti-tumor Test for Inhibitors of the EML4-ALK Fusion Polypeptide v3 Against NCI-H2228

$3\times10^6$ cells of NCI-H2228 suspended in 50% BD Matrigel™ (BD Biosciences) in PBS were inoculated subcutaneously by injection to the back of 5 weeks old male NOD/SCID mice (Japan Charles River Inc.). After 3 weeks of the inoculation, the administration of compound C, an inhibitor of the EML4-ALK fusion polypeptide v3, was initiated. The test was conducted in the solvent group and compound C group, 6 animals per group. Compound C was dissolved in a solvent composed of 10% 1-methyl-2-pyrrolidinone (SIGMA-ALDRICH Inc.)/90% polyethylene glycol 300 (Fluka Inc.) and administered orally at the dose of 10 mg/kg. Administrations were performed once a day for 14 days, and body weight and tumor size were measured every three or four day. Tumor volume was calculated using the following formula.

[Tumor volume (mm$^3$)]=[Tumor major axis (mm)]×[tumor minor axis (mm)]$^2$×0.5

Assuming the tumor volume of the solvent group on the day of starting and the day of finishing administration was 100% inhibition and 0% inhibition, respectively, the inhibition rate of compound C was calculated. The results indicated that compound C inhibited the growth of NCI-H2228 by 132%.

From the above results, it became clear that inhibitor against the EML4-ALK fusion polynucleotide v3 was useful as a therapeutic agent for the polynucleotide of the present invention—positive lung cancer patients.

What is claimed is:

1. An isolated polynucleotide encoding a polypeptide comprising the amino acid sequence of SEQ ID NO: 1.

2. An expression vector comprising the polynucleotide according to claim 1.

3. An isolated cell transformed with the expression vector according to claim 2.

4. A method for producing a polypeptide comprising the amino acid sequence of SEQ ID NO: 1, comprising culturing the transformed cell according to claim 3 under conditions suitable for polypeptide expression and collecting the polypeptide from the cell.

* * * * *

```
SEQUENCE LISTING

<160> NUMBER OF SEQ ID NOS: 14

<210> SEQ ID NO 1
<211> LENGTH: 796
<212> TYPE: PRT
<213> ORGANISM: Homo sapiens

<400> SEQUENCE: 1

Met Asp Gly Phe Ala Gly Ser Leu Asp Ser Ile Ser Ala Ala Ser
1               5                   10                  15

Thr Ser Asp Val Gln Asp Arg Leu Ser Ala Leu Glu Ser Arg Val Gln
                20                  25                  30

Gln Gln Glu Asp Glu Ile Thr Val Leu Lys Ala Ala Leu Ala Asp Val
            35                  40                  45

Leu Arg Arg Leu Ala Ile Ser Glu Asp His Val Ala Ser Val Lys Lys
    50                  55                  60

Ser Val Ser Ser Lys Gly Gln Pro Ser Pro Arg Ala Val Ile Pro Met
65                  70                  75                  80

Ser Cys Ile Thr Asn Gly Ser Gly Ala Asn Arg Lys Pro Ser His Thr
                85                  90                  95

Ser Ala Val Ser Ile Ala Gly Lys Glu Thr Leu Ser Ser Ala Ala Lys
            100                 105                 110

Ser Gly Thr Glu Lys Lys Lys Glu Lys Pro Gln Gly Gln Arg Glu Lys
        115                 120                 125

Lys Glu Glu Ser His Ser Asn Asp Gln Ser Pro Gln Ile Arg Ala Ser
    130                 135                 140

Pro Ser Pro Gln Pro Ser Ser Gln Pro Leu Gln Ile His Arg Gln Thr
145                 150                 155                 160

Pro Glu Ser Lys Asn Ala Thr Pro Thr Lys Ser Ile Lys Arg Pro Ser
                165                 170                 175

Pro Ala Glu Lys Ser His Asn Ser Trp Glu Asn Ser Asp Asp Ser Arg
            180                 185                 190

Asn Lys Leu Ser Lys Ile Pro Ser Thr Pro Lys Leu Ile Pro Lys Val
        195                 200                 205

Thr Lys Thr Ala Asp Lys His Lys Asp Val Ile Ile Asn Gln Ala Lys
    210                 215                 220

Met Ser Thr Arg Lys Lys Asn Ser Gln Val Tyr Arg Arg Lys His Gln
225                 230                 235                 240

Glu Leu Gln Ala Met Gln Met Glu Leu Gln Ser Pro Glu Tyr Lys Leu
                245                 250                 255

Ser Lys Leu Arg Thr Ser Thr Ile Met Thr Asp Tyr Asn Pro Asn Tyr
            260                 265                 270

Cys Phe Ala Gly Lys Thr Ser Ser Ile Ser Asp Leu Lys Glu Val Pro
        275                 280                 285
```

-continued

Arg Lys Asn Ile Thr Leu Ile Arg Gly Leu Gly His Gly Ala Phe Gly
    290                 295                 300

Glu Val Tyr Glu Gly Gln Val Ser Gly Met Pro Asn Asp Pro Ser Pro
305                 310                 315                 320

Leu Gln Val Ala Val Lys Thr Leu Pro Glu Val Cys Ser Glu Gln Asp
                325                 330                 335

Glu Leu Asp Phe Leu Met Glu Ala Leu Ile Ile Ser Lys Phe Asn His
                340                 345                 350

Gln Asn Ile Val Arg Cys Ile Gly Val Ser Leu Gln Ser Leu Pro Arg
            355                 360                 365

Phe Ile Leu Leu Glu Leu Met Ala Gly Gly Asp Leu Lys Ser Phe Leu
    370                 375                 380

Arg Glu Thr Arg Pro Arg Pro Ser Gln Pro Ser Ser Leu Ala Met Leu
385                 390                 395                 400

Asp Leu Leu His Val Ala Arg Asp Ile Ala Cys Gly Cys Gln Tyr Leu
                405                 410                 415

Glu Glu Asn His Phe Ile His Arg Asp Ile Ala Ala Arg Asn Cys Leu
                420                 425                 430

Leu Thr Cys Pro Gly Pro Gly Arg Val Ala Lys Ile Gly Asp Phe Gly
            435                 440                 445

Met Ala Arg Asp Ile Tyr Arg Ala Ser Tyr Tyr Arg Lys Gly Gly Cys
    450                 455                 460

Ala Met Leu Pro Val Lys Trp Met Pro Pro Glu Ala Phe Met Glu Gly
465                 470                 475                 480

Ile Phe Thr Ser Lys Thr Asp Thr Trp Ser Phe Gly Val Leu Leu Trp
                485                 490                 495

Glu Ile Phe Ser Leu Gly Tyr Met Pro Tyr Pro Ser Lys Ser Asn Gln
                500                 505                 510

Glu Val Leu Glu Phe Val Thr Ser Gly Gly Arg Met Asp Pro Pro Lys
            515                 520                 525

Asn Cys Pro Gly Pro Val Tyr Arg Ile Met Thr Gln Cys Trp Gln His
    530                 535                 540

Gln Pro Glu Asp Arg Pro Asn Phe Ala Ile Ile Leu Glu Arg Ile Glu
545                 550                 555                 560

Tyr Cys Thr Gln Asp Pro Asp Val Ile Asn Thr Ala Leu Pro Ile Glu
                565                 570                 575

Tyr Gly Pro Leu Val Glu Glu Glu Lys Val Pro Val Arg Pro Lys
                580                 585                 590

Asp Pro Glu Gly Val Pro Pro Leu Leu Val Ser Gln Gln Ala Lys Arg
            595                 600                 605

Glu Glu Glu Arg Ser Pro Ala Ala Pro Pro Pro Leu Pro Thr Thr Ser
    610                 615                 620

Ser Gly Lys Ala Ala Lys Lys Pro Thr Ala Ala Glu Val Ser Val Arg
625                 630                 635                 640

Val Pro Arg Gly Pro Ala Val Glu Gly Gly His Val Asn Met Ala Phe
                645                 650                 655

Ser Gln Ser Asn Pro Pro Ser Glu Leu His Arg Val His Gly Ser Arg
            660                 665                 670

Asn Lys Pro Thr Ser Leu Trp Asn Pro Thr Tyr Gly Ser Trp Phe Thr
    675                 680                 685

Glu Lys Pro Thr Lys Lys Asn Asn Pro Ile Ala Lys Lys Glu Pro His
690                 695                 700

-continued

```
Glu Arg Gly Asn Leu Gly Leu Glu Gly Ser Cys Thr Val Pro Pro Asn
705                 710                 715                 720

Val Ala Thr Gly Arg Leu Pro Gly Ala Ser Leu Leu Leu Glu Pro Ser
                725                 730                 735

Ser Leu Thr Ala Asn Met Lys Glu Val Pro Leu Phe Arg Leu Arg His
            740                 745                 750

Phe Pro Cys Gly Asn Val Asn Tyr Gly Tyr Gln Gln Gln Gly Leu Pro
        755                 760                 765

Leu Glu Ala Ala Thr Ala Pro Gly Ala Gly His Tyr Glu Asp Thr Ile
    770                 775                 780

Leu Lys Ser Lys Asn Ser Met Asn Gln Pro Gly Pro
785                 790                 795

<210> SEQ ID NO 2
<211> LENGTH: 2391
<212> TYPE: DNA
<213> ORGANISM: Homo sapiens
<220> FEATURE:
<221> NAME/KEY: CDS
<222> LOCATION: (1)..(2388)

<400> SEQUENCE: 2 atg gac ggt ttc gcc ggc agt ctc gat gat agt att tct gct gca agt      48
Met Asp Gly Phe Ala Gly Ser Leu Asp Asp Ser Ile Ser Ala Ala Ser
1               5                   10                  15 act tct gat gtt caa gat cgc ctg tca gct ctt gag tca cga gtt cag      96
Thr Ser Asp Val Gln Asp Arg Leu Ser Ala Leu Glu Ser Arg Val Gln
            20                  25                  30 caa caa gaa gat gaa atc act gtg cta aag gcg gct ttg gct gat gtt     144
Gln Gln Glu Asp Glu Ile Thr Val Leu Lys Ala Ala Leu Ala Asp Val
        35                  40                  45 ttg agg cgt ctt gca atc tct gaa gat cat gtg gcc tca gtg aaa aaa     192
Leu Arg Arg Leu Ala Ile Ser Glu Asp His Val Ala Ser Val Lys Lys
    50                  55                  60 tca gtc tca agt aaa ggc caa cca agc cct cga gca gtt att ccc atg     240
Ser Val Ser Ser Lys Gly Gln Pro Ser Pro Arg Ala Val Ile Pro Met
65                  70                  75                  80 tcc tgt ata acc aat gga agt ggt gca aac aga aaa cca agt cat acc     288
Ser Cys Ile Thr Asn Gly Ser Gly Ala Asn Arg Lys Pro Ser His Thr
                85                  90                  95 agt gct gtc tca att gca gga aaa gaa act ctt tca tct gct gct aaa     336
Ser Ala Val Ser Ile Ala Gly Lys Glu Thr Leu Ser Ser Ala Ala Lys
            100                 105                 110 agt ggt aca gaa aaa aag aaa gaa aaa cca caa gga cag aga gaa aaa     384
Ser Gly Thr Glu Lys Lys Lys Glu Lys Pro Gln Gly Gln Arg Glu Lys
        115                 120                 125 aaa gag gaa tct cat tct aat gat caa agt cca caa att cga gca tca     432
Lys Glu Glu Ser His Ser Asn Asp Gln Ser Pro Gln Ile Arg Ala Ser
    130                 135                 140 cct tct ccc cag ccc tct tca caa cct ctc caa ata cac aga caa act     480
Pro Ser Pro Gln Pro Ser Ser Gln Pro Leu Gln Ile His Arg Gln Thr
145                 150                 155                 160 cca gaa agc aag aat gct act ccc acc aaa agc ata aaa cga cca tca     528
Pro Glu Ser Lys Asn Ala Thr Pro Thr Lys Ser Ile Lys Arg Pro Ser
                165                 170                 175 cca gct gaa aag tca cat aat tct tgg gaa aat tca gat gat agc cgt     576
Pro Ala Glu Lys Ser His Asn Ser Trp Glu Asn Ser Asp Asp Ser Arg
            180                 185                 190 aat aaa ttg tcg aaa ata cct tca aca ccc aaa tta ata cca aaa gtt     624
Asn Lys Leu Ser Lys Ile Pro Ser Thr Pro Lys Leu Ile Pro Lys Val
```

```
                    195                 200                 205
acc aaa act gca gac aag cat aaa gat gtc atc atc aac caa gca aaa        672
Thr Lys Thr Ala Asp Lys His Lys Asp Val Ile Ile Asn Gln Ala Lys
    210                 215                 220 atg tca act cgc aaa aaa aac agc caa gtg tac cgc cgg aag cac cag        720
Met Ser Thr Arg Lys Lys Asn Ser Gln Val Tyr Arg Arg Lys His Gln
225                 230                 235                 240 gag ctg caa gcc atg cag atg gag ctg cag agc cct gag tac aag ctg        768
Glu Leu Gln Ala Met Gln Met Glu Leu Gln Ser Pro Glu Tyr Lys Leu
                245                 250                 255 agc aag ctc cgc acc tcg acc atc atg acc gac tac aac ccc aac tac        816
Ser Lys Leu Arg Thr Ser Thr Ile Met Thr Asp Tyr Asn Pro Asn Tyr
            260                 265                 270 tgc ttt gct ggc aag acc tcc tcc atc agt gac ctg aag gag gtg ccg        864
Cys Phe Ala Gly Lys Thr Ser Ser Ile Ser Asp Leu Lys Glu Val Pro
        275                 280                 285 cgg aaa aac atc acc ctc att cgg ggt ctg ggc cat gga gcc ttt ggg        912
Arg Lys Asn Ile Thr Leu Ile Arg Gly Leu Gly His Gly Ala Phe Gly
    290                 295                 300 gag gtg tat gaa ggc cag gtg tcc gga atg ccc aac gac cca agc ccc        960
Glu Val Tyr Glu Gly Gln Val Ser Gly Met Pro Asn Asp Pro Ser Pro
305                 310                 315                 320 ctg caa gtg gct gtg aag acg ctg cct gaa gtg tgc tct gaa cag gac       1008
Leu Gln Val Ala Val Lys Thr Leu Pro Glu Val Cys Ser Glu Gln Asp
                325                 330                 335 gaa ctg gat ttc ctc atg gaa gcc ctg atc atc agc aaa ttc aac cac       1056
Glu Leu Asp Phe Leu Met Glu Ala Leu Ile Ile Ser Lys Phe Asn His
            340                 345                 350 cag aac att gtt cgc tgc att ggg gtg agc ctg caa tcc ctg ccc cgg       1104
Gln Asn Ile Val Arg Cys Ile Gly Val Ser Leu Gln Ser Leu Pro Arg
        355                 360                 365 ttc atc ctg ctg gag ctc atg gcg ggg gga gac ctc aag tcc ttc ctc       1152
Phe Ile Leu Leu Glu Leu Met Ala Gly Gly Asp Leu Lys Ser Phe Leu
    370                 375                 380 cga gag acc cgc cct cgc ccg agc cag ccc tcc tcc ctg gcc atg ctg       1200
Arg Glu Thr Arg Pro Arg Pro Ser Gln Pro Ser Ser Leu Ala Met Leu
385                 390                 395                 400 gac ctt ctg cac gtg gct cgg gac att gcc tgt ggc tgt cag tat ttg       1248
Asp Leu Leu His Val Ala Arg Asp Ile Ala Cys Gly Cys Gln Tyr Leu
                405                 410                 415 gag gaa aac cac ttc atc cac cga gac att gct gcc aga aac tgc ctc       1296
Glu Glu Asn His Phe Ile His Arg Asp Ile Ala Ala Arg Asn Cys Leu
            420                 425                 430 ttg acc tgt cca ggc cct gga aga gtg gcc aag att gga gac ttc ggg       1344
Leu Thr Cys Pro Gly Pro Gly Arg Val Ala Lys Ile Gly Asp Phe Gly
        435                 440                 445 atg gcc cga gac atc tac agg gcg agc tac tat aga aag gga ggc tgt       1392
Met Ala Arg Asp Ile Tyr Arg Ala Ser Tyr Tyr Arg Lys Gly Gly Cys
    450                 455                 460 gcc atg ctg cca gtt aag tgg atg ccc cca gag gcc ttc atg gaa gga       1440
Ala Met Leu Pro Val Lys Trp Met Pro Pro Glu Ala Phe Met Glu Gly
465                 470                 475                 480 ata ttc act tct aaa aca gac aca tgg tcc ttt gga gtg ctg cta tgg       1488
Ile Phe Thr Ser Lys Thr Asp Thr Trp Ser Phe Gly Val Leu Leu Trp
                485                 490                 495 gaa atc ttt tct ctt gga tat atg cca tac ccc agc aaa agc aac cag       1536
Glu Ile Phe Ser Leu Gly Tyr Met Pro Tyr Pro Ser Lys Ser Asn Gln
            500                 505                 510 gaa gtt ctg gag ttt gtc acc agt gga ggc cgg atg gac cca ccc aag       1584
```

```
                Glu Val Leu Glu Phe Val Thr Ser Gly Gly Arg Met Asp Pro Pro Lys
                    515                 520                 525 aac tgc cct ggg cct gta tac cgg ata atg act cag tgc tgg caa cat          1632
Asn Cys Pro Gly Pro Val Tyr Arg Ile Met Thr Gln Cys Trp Gln His
            530                 535                 540 cag cct gaa gac agg ccc aac ttt gcc atc att ttg gag agg att gaa          1680
Gln Pro Glu Asp Arg Pro Asn Phe Ala Ile Ile Leu Glu Arg Ile Glu
545                 550                 555                 560 tac tgc acc cag gac ccg gat gta atc aac acc gct ttg ccg ata gaa          1728
Tyr Cys Thr Gln Asp Pro Asp Val Ile Asn Thr Ala Leu Pro Ile Glu
                565                 570                 575 tat ggt cca ctt gtg gaa gag gaa gag aaa gtg cct gtg agg ccc aag          1776
Tyr Gly Pro Leu Val Glu Glu Glu Glu Lys Val Pro Val Arg Pro Lys
            580                 585                 590 gac cct gag ggg gtt cct cct ctc ctg gtc tct caa cag gca aaa cgg          1824
Asp Pro Glu Gly Val Pro Pro Leu Leu Val Ser Gln Gln Ala Lys Arg
595                 600                 605 gag gag gag cgc agc cca gct gcc cca cca cct ctg cct acc acc tcc          1872
Glu Glu Glu Arg Ser Pro Ala Ala Pro Pro Pro Leu Pro Thr Thr Ser
        610                 615                 620 tct ggc aag gct gca aag aaa ccc aca gct gca gag gtc tct gtt cga          1920
Ser Gly Lys Ala Ala Lys Lys Pro Thr Ala Ala Glu Val Ser Val Arg
625                 630                 635                 640 gtc cct aga ggg ccg gcc gtg gaa ggg gga cac gtg aat atg gca ttc          1968
Val Pro Arg Gly Pro Ala Val Glu Gly Gly His Val Asn Met Ala Phe
                645                 650                 655 tct cag tcc aac cct cct tcg gag ttg cac agg gtc cac gga tcc aga          2016
Ser Gln Ser Asn Pro Pro Ser Glu Leu His Arg Val His Gly Ser Arg
            660                 665                 670 aac aag ccc acc agc ttg tgg aac cca acg tac ggc tcc tgg ttt aca          2064
Asn Lys Pro Thr Ser Leu Trp Asn Pro Thr Tyr Gly Ser Trp Phe Thr
        675                 680                 685 gag aaa ccc acc aaa aag aat aat cct ata gca aag aag gag cca cac          2112
Glu Lys Pro Thr Lys Lys Asn Asn Pro Ile Ala Lys Lys Glu Pro His
690                 695                 700 gag agg ggt aac ctg ggg ctg gag gga agc tgt act gtc cca cct aac          2160
Glu Arg Gly Asn Leu Gly Leu Glu Gly Ser Cys Thr Val Pro Pro Asn
            705                 710                 715                 720 gtt gca act ggg aga ctt ccg ggg gcc tca ctg ctc cta gag ccc tct          2208
Val Ala Thr Gly Arg Leu Pro Gly Ala Ser Leu Leu Leu Glu Pro Ser
                725                 730                 735 tcg ctg act gcc aat atg aag gag gta cct ctg ttc agg cta cgt cac          2256
Ser Leu Thr Ala Asn Met Lys Glu Val Pro Leu Phe Arg Leu Arg His
            740                 745                 750 ttc cct tgt ggg aat gtc aat tac ggc tac cag caa cag ggc ttg ccc          2304
Phe Pro Cys Gly Asn Val Asn Tyr Gly Tyr Gln Gln Gln Gly Leu Pro
        755                 760                 765 tta gaa gcc gct act gcc cct gga gct ggt cat tac gag gat acc att          2352
Leu Glu Ala Ala Thr Ala Pro Gly Ala Gly His Tyr Glu Asp Thr Ile
770                 775                 780 ctg aaa agc aag aat agc atg aac cag cct ggg ccc tga                      2391
Leu Lys Ser Lys Asn Ser Met Asn Gln Pro Gly Pro
785                 790                 795

<210> SEQ ID NO 3
<211> LENGTH: 24
<212> TYPE: DNA
<213> ORGANISM: Homo sapiens

<400> SEQUENCE: 3
```

```
taccagtgct gtctcaattg cagg                                          24

<210> SEQ ID NO 4
<211> LENGTH: 24
<212> TYPE: DNA
<213> ORGANISM: Homo sapiens

<400> SEQUENCE: 4
tcttgccagc aaagcagtag ttgg                                          24

<210> SEQ ID NO 5
<211> LENGTH: 515
<212> TYPE: DNA
<213> ORGANISM: Homo sapiens

<400> SEQUENCE: 5
taccagtgct gtctcaattg caggaaaaga aactctttca tctgctgcta aaagtggtac   60
agaaaaaaag aaagaaaaac cacaaggaca gagagaaaaa aaagaggaat ctcattctaa  120
tgatcaaagt ccacaaattc gagcatcacc ttctccccag ccctcttcac aacctctcca  180
aatacacaga caaactccag aaagcaagaa tgctactccc accaaaagca taaaacgacc  240
atcaccagct gaaaagtcac ataattcttg ggaaaattca gatgatagcc gtaataaatt  300
gtcgaaaata ccttcaacac ccaaattaat accaaaagtt accaaaactg cagacaagca  360
taaagatgtc atcatcaacc aagtgtaccg ccggaagcac caggagctgc aagccatgca  420
gatggagctg cagagccctg agtacaagct gagcaagctc cgcacctcga ccatcatgac  480
cgactacaac cccaactact gctttgctgg caaga                             515

<210> SEQ ID NO 6
<211> LENGTH: 548
<212> TYPE: DNA
<213> ORGANISM: Homo sapiens

<400> SEQUENCE: 6
taccagtgct gtctcaattg caggaaaaga aactctttca tctgctgcta aaagtggtac   60
agaaaaaaag aaagaaaaac cacaaggaca gagagaaaaa aaagaggaat ctcattctaa  120
tgatcaaagt ccacaaattc gagcatcacc ttctccccag ccctcttcac aacctctcca  180
aatacacaga caaactccag aaagcaagaa tgctactccc accaaaagca taaaacgacc  240
atcaccagct gaaaagtcac ataattcttg ggaaaattca gatgatagcc gtaataaatt  300
gtcgaaaata ccttcaacac ccaaattaat accaaaagtt accaaaactg cagacaagca  360
taaagatgtc atcatcaacc aagcaaaaat gtcaactcgc aaaaaaaaca gccaagtgta  420
ccgccggaag caccaggagc tgcaagccat gcagatggag ctgcagagcc tgagtacaa   480 gctgagcaag ctccgcacct cgaccatcat gaccgactac aaccccaact actgctttgc  540
tggcaaga                                                           548

<210> SEQ ID NO 7
<211> LENGTH: 24
<212> TYPE: DNA
<213> ORGANISM: Homo sapiens

<400> SEQUENCE: 7
actctgtcgg tccgctgaat gaag                                          24

<210> SEQ ID NO 8
<211> LENGTH: 23
```

<212> TYPE: DNA
<213> ORGANISM: Homo sapiens

<400> SEQUENCE: 8
ccacggtctt agggatccca agg    23

<210> SEQ ID NO 9
<211> LENGTH: 30
<212> TYPE: DNA
<213> ORGANISM: Artificial Sequence
<220> FEATURE:
<223> OTHER INFORMATION: synthetic oligonucleotide primer

<400> SEQUENCE: 9
aagcttatgg acggtttcgc cggcagtctc    30

<210> SEQ ID NO 10
<211> LENGTH: 24
<212> TYPE: DNA
<213> ORGANISM: Artificial Sequence
<220> FEATURE:
<223> OTHER INFORMATION: synthetic oligonucleotide primer

<400> SEQUENCE: 10
tctagatcag ggcccaggct ggtt    24

<210> SEQ ID NO 11
<211> LENGTH: 2391
<212> TYPE: DNA
<213> ORGANISM: Homo sapiens
<220> FEATURE:
<221> NAME/KEY: CDS
<222> LOCATION: (1)..(2388)

<400> SEQUENCE: 11

```
atg gac ggt ttc gcc ggc agt ctc gat gat agt att tct gct gca agt       48
Met Asp Gly Phe Ala Gly Ser Leu Asp Asp Ser Ile Ser Ala Ala Ser
1               5                   10                  15 act tct gat gtt caa gat cgc ctg tca gct ctt gag tca cga gtt cag       96
Thr Ser Asp Val Gln Asp Arg Leu Ser Ala Leu Glu Ser Arg Val Gln
            20                  25                  30 caa caa gaa gat gaa atc act gtg cta aag gcg gct ttg gct gat gtt      144
Gln Gln Glu Asp Glu Ile Thr Val Leu Lys Ala Ala Leu Ala Asp Val
        35                  40                  45 ttg agg cgt ctt gca atc tct gaa gat cat gtg gcc tca gtg aaa aaa      192
Leu Arg Arg Leu Ala Ile Ser Glu Asp His Val Ala Ser Val Lys Lys
    50                  55                  60 tca gtc tca agt aaa ggc caa cca agc cct cga gca gtt att ccc atg      240
Ser Val Ser Ser Lys Gly Gln Pro Ser Pro Arg Ala Val Ile Pro Met
65                  70                  75                  80 tcc tgt ata acc aat gga agt ggt gca aac aga aaa cca agt cat acc      288
Ser Cys Ile Thr Asn Gly Ser Gly Ala Asn Arg Lys Pro Ser His Thr
                85                  90                  95 agt gct gtc tca att gca gga aaa gaa act ctt tca tct gct gct aaa      336
Ser Ala Val Ser Ile Ala Gly Lys Glu Thr Leu Ser Ser Ala Ala Lys
            100                 105                 110 agt ggt aca gaa aaa aag aaa gaa aaa cca caa gga cag aga gaa aaa      384
Ser Gly Thr Glu Lys Lys Lys Glu Lys Pro Gln Gly Gln Arg Glu Lys
        115                 120                 125 aaa gag gaa tct cat tct aat gat caa agt cca caa att cga gca tca      432
Lys Glu Glu Ser His Ser Asn Asp Gln Ser Pro Gln Ile Arg Ala Ser
    130                 135                 140 cct tct ccc cag ccc tct tca caa cct ctc caa ata cac aga caa act      480
```

```
                                                              -continued

Pro Ser Pro Gln Pro Ser Ser Gln Pro Leu Gln Ile His Arg Gln Thr
145             150                 155                 160 cca gaa agc aag aat gct act ccc acc aaa agc ata aaa cga cca tca       528
Pro Glu Ser Lys Asn Ala Thr Pro Thr Lys Ser Ile Lys Arg Pro Ser
                165                 170                 175 cca gct gaa aag tca cat aat tct tgg gaa aat tca gat gat agc cgt       576
Pro Ala Glu Lys Ser His Asn Ser Trp Glu Asn Ser Asp Asp Ser Arg
            180                 185                 190 aat aaa ttg tcg aaa ata cct tca aca ccc aaa tta ata cca aaa gtt       624
Asn Lys Leu Ser Lys Ile Pro Ser Thr Pro Lys Leu Ile Pro Lys Val
        195                 200                 205 acc aaa act gca gac aag cat aaa gat gtc atc atc aac caa gca aaa       672
Thr Lys Thr Ala Asp Lys His Lys Asp Val Ile Ile Asn Gln Ala Lys
    210                 215                 220 atg tca act cgc gaa aaa aac agc caa gtg tac cgc cgg aag cac cag       720
Met Ser Thr Arg Glu Lys Asn Ser Gln Val Tyr Arg Arg Lys His Gln
225                 230                 235                 240 gag ctg caa gcc atg cag atg gag ctg cag agc cct gag tac aag ctg       768
Glu Leu Gln Ala Met Gln Met Glu Leu Gln Ser Pro Glu Tyr Lys Leu
                245                 250                 255 agc aag ctc cgc acc tcg acc atc atg acc gac tac aac ccc aac tac       816
Ser Lys Leu Arg Thr Ser Thr Ile Met Thr Asp Tyr Asn Pro Asn Tyr
            260                 265                 270 tgc ttt gct ggc aag acc tcc tcc atc agt gac ctg aag gag gtg ccg       864
Cys Phe Ala Gly Lys Thr Ser Ser Ile Ser Asp Leu Lys Glu Val Pro
        275                 280                 285 cgg aaa aac atc acc ctc att cgg ggt ctg ggc cat ggc gcc ttt ggg       912
Arg Lys Asn Ile Thr Leu Ile Arg Gly Leu Gly His Gly Ala Phe Gly
    290                 295                 300 gag gtg tat gaa ggc cag gtg tcc gga atg ccc aac gac cca agc ccc       960
Glu Val Tyr Glu Gly Gln Val Ser Gly Met Pro Asn Asp Pro Ser Pro
305                 310                 315                 320 ctg caa gtg gct gtg aag acg ctg cct gaa gtg tgc tct gaa cag gac      1008
Leu Gln Val Ala Val Lys Thr Leu Pro Glu Val Cys Ser Glu Gln Asp
                325                 330                 335 gaa ctg gat ttc ctc atg gaa gcc ctg atc atc agc aaa ttc aac cac      1056
Glu Leu Asp Phe Leu Met Glu Ala Leu Ile Ile Ser Lys Phe Asn His
            340                 345                 350 cag aac att gtt cgc tgc att ggg gtg agc ctg caa tcc ctg ccc cgg      1104
Gln Asn Ile Val Arg Cys Ile Gly Val Ser Leu Gln Ser Leu Pro Arg
        355                 360                 365 ttc atc ctg ctg gag ctc atg gcg ggg gga gac ctc aag tcc ttc ctc      1152
Phe Ile Leu Leu Glu Leu Met Ala Gly Gly Asp Leu Lys Ser Phe Leu
    370                 375                 380 cga gag acc cgc cct cgc ccg agc cag ccc tcc tcc ctg gcc atg ctg      1200
Arg Glu Thr Arg Pro Arg Pro Ser Gln Pro Ser Ser Leu Ala Met Leu
385                 390                 395                 400 gac ctt ctg cac gtg gct cgg gac att gcc tgt ggc tgt cag tat ttg      1248
Asp Leu Leu His Val Ala Arg Asp Ile Ala Cys Gly Cys Gln Tyr Leu
                405                 410                 415 gag gaa aac cac ttc atc cac cga gac att gct gcc aga aac tgc ctc      1296
Glu Glu Asn His Phe Ile His Arg Asp Ile Ala Ala Arg Asn Cys Leu
            420                 425                 430 ttg acc tgt cca ggc cct gga aga gtg gcc aag att gga gac ttc ggg      1344
Leu Thr Cys Pro Gly Pro Gly Arg Val Ala Lys Ile Gly Asp Phe Gly
        435                 440                 445 atg gcc cga gac atc tac agg gcg agc tac tat aga aag gga ggc tgt      1392
Met Ala Arg Asp Ile Tyr Arg Ala Ser Tyr Tyr Arg Lys Gly Gly Cys
    450                 455                 460
```

```
gcc atg ctg cca gtt aag tgg atg ccc cca gag gcc ttc atg gaa gga    1440
Ala Met Leu Pro Val Lys Trp Met Pro Pro Glu Ala Phe Met Glu Gly
465                 470                 475                 480 ata ttc act tct aaa aca gac aca tgg tcc ttt gga gtg ctg cta tgg    1488
Ile Phe Thr Ser Lys Thr Asp Thr Trp Ser Phe Gly Val Leu Leu Trp
                485                 490                 495 gaa atc ttt tct ctt gga tat atg cca tac ccc agc aaa agc aac cag    1536
Glu Ile Phe Ser Leu Gly Tyr Met Pro Tyr Pro Ser Lys Ser Asn Gln
                500                 505                 510 gaa gtt ctg gag ttt gtc acc agt gga ggc cgg atg gac cca ccc aag    1584
Glu Val Leu Glu Phe Val Thr Ser Gly Gly Arg Met Asp Pro Pro Lys
            515                 520                 525 aac tgc cct ggg cct gta tac cgg ata atg act cag tgc tgg caa cat    1632
Asn Cys Pro Gly Pro Val Tyr Arg Ile Met Thr Gln Cys Trp Gln His
    530                 535                 540 cag cct gaa gac agg ccc aac ttt gcc atc att ttg gag agg att gaa    1680
Gln Pro Glu Asp Arg Pro Asn Phe Ala Ile Ile Leu Glu Arg Ile Glu
545                 550                 555                 560 tac tgc acc cag gac ccg gat gta atc aac acc gct ttg ccg ata gaa    1728
Tyr Cys Thr Gln Asp Pro Asp Val Ile Asn Thr Ala Leu Pro Ile Glu
                565                 570                 575 tat ggt cca ctt gtg gaa gag gaa gag aaa gtg cct gtg agg ccc aag    1776
Tyr Gly Pro Leu Val Glu Glu Glu Glu Lys Val Pro Val Arg Pro Lys
                580                 585                 590 gac cct gag ggg gtt cct cct ctc ctg gtc tct caa cag gca aaa cgg    1824
Asp Pro Glu Gly Val Pro Pro Leu Leu Val Ser Gln Gln Ala Lys Arg
            595                 600                 605 gag gag gag cgc agc cca gct gcc cca cca cct ctg cct acc acc tcc    1872
Glu Glu Glu Arg Ser Pro Ala Ala Pro Pro Pro Leu Pro Thr Thr Ser
    610                 615                 620 tct ggc aag gct gca aag aaa ccc aca gct gca gag gtc tct gtt cga    1920
Ser Gly Lys Ala Ala Lys Lys Pro Thr Ala Ala Glu Val Ser Val Arg
625                 630                 635                 640 gtc cct aga ggg ccg gcc gtg aaa ggg gga cac gtg aat atg gca ttc    1968
Val Pro Arg Gly Pro Ala Val Glu Gly Gly His Val Asn Met Ala Phe
                645                 650                 655 tct cag tcc aac cct cct tcg gag ttg cac aag gtc cac gga tcc aga    2016
Ser Gln Ser Asn Pro Pro Ser Glu Leu His Lys Val His Gly Ser Arg
                660                 665                 670 aac aag ccc acc agc ttg tgg aac cca acg tac ggc tcc tgg ttt aca    2064
Asn Lys Pro Thr Ser Leu Trp Asn Pro Thr Tyr Gly Ser Trp Phe Thr
            675                 680                 685 gag aaa ccc acc aaa aag aat aat cct ata gca aag aag gag cca cac    2112
Glu Lys Pro Thr Lys Lys Asn Asn Pro Ile Ala Lys Lys Glu Pro His
    690                 695                 700 gac agg ggt aac ctg ggg ctg gag gga agc tgt act gtc cca cct aac    2160
Asp Arg Gly Asn Leu Gly Leu Glu Gly Ser Cys Thr Val Pro Pro Asn
705                 710                 715                 720 gtt gca act ggg aga ctt ccg ggg gcc tca ctg ctc cta gag ccc tct    2208
Val Ala Thr Gly Arg Leu Pro Gly Ala Ser Leu Leu Leu Glu Pro Ser
                725                 730                 735 tcg ctg act gcc aat atg aag gag gta cct ctg ttc agg cta cgt cac    2256
Ser Leu Thr Ala Asn Met Lys Glu Val Pro Leu Phe Arg Leu Arg His
                740                 745                 750 ttc cct tgt ggg aat gtc aat tac ggc tac cag caa cag ggc ttg ccc    2304
Phe Pro Cys Gly Asn Val Asn Tyr Gly Tyr Gln Gln Gln Gly Leu Pro
            755                 760                 765 tta gaa gcc gct act gcc cct gga gct ggt cat tac gag gat acc att    2352
Leu Glu Ala Ala Thr Ala Pro Gly Ala Gly His Tyr Glu Asp Thr Ile
770                 775                 780
```

```
ctg aaa agc aag aat agc atg aac cag cct ggg ccc tga              2391
Leu Lys Ser Lys Asn Ser Met Asn Gln Pro Gly Pro
785                 790                 795
```

<210> SEQ ID NO 12
<211> LENGTH: 796
<212> TYPE: PRT
<213> ORGANISM: Homo sapiens

<400> SEQUENCE: 12

```
Met Asp Gly Phe Ala Gly Ser Leu Asp Asp Ser Ile Ser Ala Ala Ser
1               5                   10                  15

Thr Ser Asp Val Gln Asp Arg Leu Ser Ala Leu Glu Ser Arg Val Gln
            20                  25                  30

Gln Gln Glu Asp Glu Ile Thr Val Leu Lys Ala Ala Leu Ala Asp Val
        35                  40                  45

Leu Arg Arg Leu Ala Ile Ser Glu Asp His Val Ala Ser Val Lys Lys
50                  55                  60

Ser Val Ser Ser Lys Gly Gln Pro Ser Pro Arg Ala Val Ile Pro Met
65                  70                  75                  80

Ser Cys Ile Thr Asn Gly Ser Gly Ala Asn Arg Lys Pro Ser His Thr
                85                  90                  95

Ser Ala Val Ser Ile Ala Gly Lys Glu Thr Leu Ser Ser Ala Ala Lys
            100                 105                 110

Ser Gly Thr Glu Lys Lys Lys Glu Lys Pro Gln Gly Gln Arg Glu Lys
        115                 120                 125

Lys Glu Glu Ser His Ser Asn Asp Gln Ser Pro Gln Ile Arg Ala Ser
    130                 135                 140

Pro Ser Pro Gln Pro Ser Ser Gln Pro Leu Gln Ile His Arg Gln Thr
145                 150                 155                 160

Pro Glu Ser Lys Asn Ala Thr Pro Thr Lys Ser Ile Lys Arg Pro Ser
                165                 170                 175

Pro Ala Glu Lys Ser His Asn Ser Trp Glu Asn Ser Asp Asp Ser Arg
            180                 185                 190

Asn Lys Leu Ser Lys Ile Pro Ser Thr Pro Lys Leu Ile Pro Lys Val
        195                 200                 205

Thr Lys Thr Ala Asp Lys His Lys Asp Val Ile Ile Asn Gln Ala Lys
    210                 215                 220

Met Ser Thr Arg Glu Lys Asn Ser Gln Val Tyr Arg Arg Lys His Gln
225                 230                 235                 240

Glu Leu Gln Ala Met Gln Met Glu Leu Gln Ser Pro Glu Tyr Lys Leu
                245                 250                 255

Ser Lys Leu Arg Thr Ser Thr Ile Met Thr Asp Tyr Asn Pro Asn Tyr
            260                 265                 270

Cys Phe Ala Gly Lys Thr Ser Ser Ile Ser Asp Leu Lys Glu Val Pro
        275                 280                 285

Arg Lys Asn Ile Thr Leu Ile Arg Gly Leu Gly His Gly Ala Phe Gly
    290                 295                 300

Glu Val Tyr Glu Gly Gln Val Ser Gly Met Pro Asn Asp Pro Ser Pro
305                 310                 315                 320

Leu Gln Val Ala Val Lys Thr Leu Pro Glu Val Cys Ser Glu Gln Asp
                325                 330                 335

Glu Leu Asp Phe Leu Met Glu Ala Leu Ile Ile Ser Lys Phe Asn His
            340                 345                 350
```

```
Gln Asn Ile Val Arg Cys Ile Gly Val Ser Leu Gln Ser Leu Pro Arg
            355                 360                 365

Phe Ile Leu Glu Leu Met Ala Gly Gly Asp Leu Lys Ser Phe Leu
370                 375                 380

Arg Glu Thr Arg Pro Arg Pro Ser Gln Pro Ser Ser Leu Ala Met Leu
385                 390                 395                 400

Asp Leu Leu His Val Ala Arg Asp Ile Ala Cys Gly Cys Gln Tyr Leu
                405                 410                 415

Glu Glu Asn His Phe Ile His Arg Asp Ile Ala Ala Arg Asn Cys Leu
                420                 425                 430

Leu Thr Cys Pro Gly Pro Gly Arg Val Ala Lys Ile Gly Asp Phe Gly
            435                 440                 445

Met Ala Arg Asp Ile Tyr Arg Ala Ser Tyr Tyr Arg Lys Gly Gly Cys
450                 455                 460

Ala Met Leu Pro Val Lys Trp Met Pro Pro Glu Ala Phe Met Glu Gly
465                 470                 475                 480

Ile Phe Thr Ser Lys Thr Asp Thr Trp Ser Phe Gly Val Leu Leu Trp
                485                 490                 495

Glu Ile Phe Ser Leu Gly Tyr Met Pro Tyr Pro Ser Lys Ser Asn Gln
                500                 505                 510

Glu Val Leu Glu Phe Val Thr Ser Gly Gly Arg Met Asp Pro Pro Lys
                515                 520                 525

Asn Cys Pro Gly Pro Val Tyr Arg Ile Met Thr Gln Cys Trp Gln His
            530                 535                 540

Gln Pro Glu Asp Arg Pro Asn Phe Ala Ile Ile Leu Glu Arg Ile Glu
545                 550                 555                 560

Tyr Cys Thr Gln Asp Pro Asp Val Ile Asn Thr Ala Leu Pro Ile Glu
                565                 570                 575

Tyr Gly Pro Leu Val Glu Glu Glu Lys Val Pro Val Arg Pro Lys
            580                 585                 590

Asp Pro Glu Gly Val Pro Pro Leu Leu Val Ser Gln Gln Ala Lys Arg
                595                 600                 605

Glu Glu Glu Arg Ser Pro Ala Ala Pro Pro Pro Leu Pro Thr Thr Ser
        610                 615                 620

Ser Gly Lys Ala Ala Lys Lys Pro Thr Ala Ala Glu Val Ser Val Arg
625                 630                 635                 640

Val Pro Arg Gly Pro Ala Val Glu Gly Gly His Val Asn Met Ala Phe
            645                 650                 655

Ser Gln Ser Asn Pro Pro Ser Glu Leu His Lys Val His Gly Ser Arg
            660                 665                 670

Asn Lys Pro Thr Ser Leu Trp Asn Pro Thr Tyr Gly Ser Trp Phe Thr
            675                 680                 685

Glu Lys Pro Thr Lys Lys Asn Asn Pro Ile Ala Lys Lys Glu Pro His
        690                 695                 700

Asp Arg Gly Asn Leu Gly Leu Glu Gly Ser Cys Thr Val Pro Pro Asn
705                 710                 715                 720

Val Ala Thr Gly Arg Leu Pro Gly Ala Ser Leu Leu Leu Glu Pro Ser
                725                 730                 735

Ser Leu Thr Ala Asn Met Lys Glu Val Pro Leu Phe Arg Leu Arg His
            740                 745                 750

Phe Pro Cys Gly Asn Val Asn Tyr Gly Tyr Gln Gln Gln Gly Leu Pro
            755                 760                 765

Leu Glu Ala Ala Thr Ala Pro Gly Ala Gly His Tyr Glu Asp Thr Ile
```

```
                    770                 775                 780
Leu Lys Ser Lys Asn Ser Met Asn Gln Pro Gly Pro
785                 790                 795

<210> SEQ ID NO 13
<211> LENGTH: 2358
<212> TYPE: DNA
<213> ORGANISM: Homo sapiens
<220> FEATURE:
<221> NAME/KEY: CDS
<222> LOCATION: (1)..(2355)

<400> SEQUENCE: 13 atg gac ggt ttc gcc ggc agt ctc gat gat agt att tct gct gca agt      48
Met Asp Gly Phe Ala Gly Ser Leu Asp Asp Ser Ile Ser Ala Ala Ser
1               5                   10                  15 act tct gat gtt caa gat cgc ctg tca gct ctt gag tca cga gtt cag      96
Thr Ser Asp Val Gln Asp Arg Leu Ser Ala Leu Glu Ser Arg Val Gln
            20                  25                  30 caa caa gaa gat gaa atc act gtg cta aag gcg gct ttg gct gat gtt     144
Gln Gln Glu Asp Glu Ile Thr Val Leu Lys Ala Ala Leu Ala Asp Val
        35                  40                  45 ttg agg cgt ctt gca atc tct gaa gat cat gtg gcc tca gtg aaa aaa     192
Leu Arg Arg Leu Ala Ile Ser Glu Asp His Val Ala Ser Val Lys Lys
    50                  55                  60 tca gtc tca agt aaa ggc caa cca agc cct cga gca gtt att ccc atg     240
Ser Val Ser Ser Lys Gly Gln Pro Ser Pro Arg Ala Val Ile Pro Met
65                  70                  75                  80 tcc tgt ata acc aat gga agt ggt gca aac aga aaa cca agt cat acc     288
Ser Cys Ile Thr Asn Gly Ser Gly Ala Asn Arg Lys Pro Ser His Thr
                85                  90                  95 agt gct gtc tca att gca gga aaa gaa act ctt tca tct gct gct aaa     336
Ser Ala Val Ser Ile Ala Gly Lys Glu Thr Leu Ser Ser Ala Ala Lys
            100                 105                 110 agt ggt aca gaa aaa aag aaa gaa aaa cca caa gga cag aga gaa aaa     384
Ser Gly Thr Glu Lys Lys Lys Glu Lys Pro Gln Gly Gln Arg Glu Lys
        115                 120                 125 aaa gag gaa tct cat tct aat gat caa agt cca caa att cga gca tca     432
Lys Glu Glu Ser His Ser Asn Asp Gln Ser Pro Gln Ile Arg Ala Ser
    130                 135                 140 cct tct ccc cag ccc tct tca caa cct ctc caa ata cac aga caa act     480
Pro Ser Pro Gln Pro Ser Ser Gln Pro Leu Gln Ile His Arg Gln Thr
145                 150                 155                 160 cca gaa agc aag aat gct act ccc acc aaa agc ata aaa cga cca tca     528
Pro Glu Ser Lys Asn Ala Thr Pro Thr Lys Ser Ile Lys Arg Pro Ser
                165                 170                 175 cca gct gaa aag tca cat aat tct tgg gaa aat tca gat gat agc cgt     576
Pro Ala Glu Lys Ser His Asn Ser Trp Glu Asn Ser Asp Asp Ser Arg
            180                 185                 190 aat aaa ttg tcg aaa ata cct tca aca ccc aaa tta ata cca aaa gtt     624
Asn Lys Leu Ser Lys Ile Pro Ser Thr Pro Lys Leu Ile Pro Lys Val
        195                 200                 205 acc aaa act gca gac aag cat aaa gat gtc atc atc aac caa gtg tac     672
Thr Lys Thr Ala Asp Lys His Lys Asp Val Ile Ile Asn Gln Val Tyr
    210                 215                 220 cgc cgg aag cac cag gag ctg caa gcc atg cag atg gag ctg cag agc     720
Arg Arg Lys His Gln Glu Leu Gln Ala Met Gln Met Glu Leu Gln Ser
225                 230                 235                 240 cct gag tac aag ctg agc aag ctc cgc acc tcg acc atc atg acc gac     768
Pro Glu Tyr Lys Leu Ser Lys Leu Arg Thr Ser Thr Ile Met Thr Asp
                245                 250                 255
```

```
tac aac ccc aac tac tgc ttt gct ggc aag acc tcc tcc atc agt gac     816
Tyr Asn Pro Asn Tyr Cys Phe Ala Gly Lys Thr Ser Ser Ile Ser Asp
        260                 265                 270 ctg aag gag gtg ccg cgg aaa aac atc acc ctc att cgg ggt ctg ggc     864
Leu Lys Glu Val Pro Arg Lys Asn Ile Thr Leu Ile Arg Gly Leu Gly
    275                 280                 285 cat ggc gcc ttt ggg gag gtg tat gaa ggc cag gtg tcc gga atg ccc     912
His Gly Ala Phe Gly Glu Val Tyr Glu Gly Gln Val Ser Gly Met Pro
290                 295                 300 aac gac cca agc ccc ctg caa gtg gct gtg aag acg ctg cct gaa gtg     960
Asn Asp Pro Ser Pro Leu Gln Val Ala Val Lys Thr Leu Pro Glu Val
305                 310                 315                 320 tgc tct gaa cag gac gaa ctg gat ttc ctc atg gaa gcc ctg atc atc    1008
Cys Ser Glu Gln Asp Glu Leu Asp Phe Leu Met Glu Ala Leu Ile Ile
            325                 330                 335 agc aaa ttc aac cac cag aac att gtt cgc tgc att ggg gtg agc ctg    1056
Ser Lys Phe Asn His Gln Asn Ile Val Arg Cys Ile Gly Val Ser Leu
        340                 345                 350 caa tcc ctg ccc cgg ttc atc ctg ctg gag ctc atg gcg ggg gga gac    1104
Gln Ser Leu Pro Arg Phe Ile Leu Leu Glu Leu Met Ala Gly Gly Asp
    355                 360                 365 ctc aag tcc ttc ctc cga gag acc cgc cct cgc ccg agc cag ccc tcc    1152
Leu Lys Ser Phe Leu Arg Glu Thr Arg Pro Arg Pro Ser Gln Pro Ser
370                 375                 380 tcc ctg gcc atg ctg gac ctt ctg cac gtg gct cgg gac att gcc tgt    1200
Ser Leu Ala Met Leu Asp Leu Leu His Val Ala Arg Asp Ile Ala Cys
385                 390                 395                 400 ggc tgt cag tat ttg gag gaa aac cac ttc atc cac cga gac att gct    1248
Gly Cys Gln Tyr Leu Glu Glu Asn His Phe Ile His Arg Asp Ile Ala
            405                 410                 415 gcc aga aac tgc ctc ttg acc tgt cca ggc cct gga aga gtg gcc aag    1296
Ala Arg Asn Cys Leu Leu Thr Cys Pro Gly Pro Gly Arg Val Ala Lys
        420                 425                 430 att gga gac ttc ggg atg gcc cga gac atc tac agg gcg agc tac tat    1344
Ile Gly Asp Phe Gly Met Ala Arg Asp Ile Tyr Arg Ala Ser Tyr Tyr
    435                 440                 445 aga aag gga ggc tgt gcc atg ctg cca gtt aag tgg atg ccc cca gag    1392
Arg Lys Gly Gly Cys Ala Met Leu Pro Val Lys Trp Met Pro Pro Glu
450                 455                 460 gcc ttc atg gaa gga ata ttc act tct aaa aca gac aca tgg tcc ttt    1440
Ala Phe Met Glu Gly Ile Phe Thr Ser Lys Thr Asp Thr Trp Ser Phe
465                 470                 475                 480 gga gtg ctg cta tgg gaa atc ttt tct ctt gga tat atg cca tac ccc    1488
Gly Val Leu Leu Trp Glu Ile Phe Ser Leu Gly Tyr Met Pro Tyr Pro
            485                 490                 495 agc aaa agc aac cag gaa gtt ctg gag ttt gtc acc agt gga ggc cgg    1536
Ser Lys Ser Asn Gln Glu Val Leu Glu Phe Val Thr Ser Gly Gly Arg
        500                 505                 510 atg gac cca ccc aag aac tgc cct ggg cct gta tac cgg ata atg act    1584
Met Asp Pro Pro Lys Asn Cys Pro Gly Pro Val Tyr Arg Ile Met Thr
    515                 520                 525 cag tgc tgg caa cat cag cct gaa gac agg ccc aac ttt gcc atc att    1632
Gln Cys Trp Gln His Gln Pro Glu Asp Arg Pro Asn Phe Ala Ile Ile
530                 535                 540 ttg gag agg att gaa tac tgc acc cag gac ccg gat gta atc aac acc    1680
Leu Glu Arg Ile Glu Tyr Cys Thr Gln Asp Pro Asp Val Ile Asn Thr
545                 550                 555                 560 gct ttg ccg ata gaa tat ggt cca ctt gtg gaa gag gaa gag aaa gtg    1728
Ala Leu Pro Ile Glu Tyr Gly Pro Leu Val Glu Glu Glu Glu Lys Val
```

```
cct gtg agg ccc aag gac cct gag ggg gtt cct cct ctc ctg gtc tct    1776
Pro Val Arg Pro Lys Asp Pro Glu Gly Val Pro Pro Leu Leu Val Ser
        580                 585                 590 caa cag gca aaa cgg gag gag gag cgc agc cca gct gcc cca cct        1824
Gln Gln Ala Lys Arg Glu Glu Glu Arg Ser Pro Ala Ala Pro Pro
    595                 600                 605 ctg cct acc acc tcc tct ggc aag gct gca aag aaa ccc aca gct gca    1872
Leu Pro Thr Thr Ser Ser Gly Lys Ala Ala Lys Lys Pro Thr Ala Ala
610                 615                 620 gag gtc tct gtt cga gtc cct aga ggg ccg gcc gtg gaa ggg gga cac    1920
Glu Val Ser Val Arg Val Pro Arg Gly Pro Ala Val Glu Gly Gly His
625                 630                 635                 640 gtg aat atg gca ttc tct cag tcc aac cct cct tcg gag ttg cac aag    1968
Val Asn Met Ala Phe Ser Gln Ser Asn Pro Pro Ser Glu Leu His Lys
                645                 650                 655 gtc cac gga tcc aga aac aag ccc acc agc ttg tgg aac cca acg tac    2016
Val His Gly Ser Arg Asn Lys Pro Thr Ser Leu Trp Asn Pro Thr Tyr
            660                 665                 670 ggc tcc tgg ttt aca gag aaa ccc acc aaa aag aat aat cct ata gca    2064
Gly Ser Trp Phe Thr Glu Lys Pro Thr Lys Lys Asn Asn Pro Ile Ala
        675                 680                 685 aag aag gag cca cac gac agg ggt aac ctg ggg ctg gag gga agc tgt    2112
Lys Lys Glu Pro His Asp Arg Gly Asn Leu Gly Leu Glu Gly Ser Cys
690                 695                 700 act gtc cca cct aac gtt gca act ggg aga ctt ccg ggg gcc tca ctg    2160
Thr Val Pro Pro Asn Val Ala Thr Gly Arg Leu Pro Gly Ala Ser Leu
705                 710                 715                 720 ctc cta gag ccc tct tcg ctg act gcc aat atg aag gag gta cct ctg    2208
Leu Leu Glu Pro Ser Ser Leu Thr Ala Asn Met Lys Glu Val Pro Leu
                725                 730                 735 ttc agg cta cgt cac ttc cct tgt ggg aat gtc aat tac ggc tac cag    2256
Phe Arg Leu Arg His Phe Pro Cys Gly Asn Val Asn Tyr Gly Tyr Gln
            740                 745                 750 caa cag ggc ttg ccc tta gaa gcc gct act gcc cct gga gct ggt cat    2304
Gln Gln Gly Leu Pro Leu Glu Ala Ala Thr Ala Pro Gly Ala Gly His
        755                 760                 765 tac gag gat acc att ctg aaa agc aag aat agc atg aac cag cct ggg    2352
Tyr Glu Asp Thr Ile Leu Lys Ser Lys Asn Ser Met Asn Gln Pro Gly
770                 775                 780 ccc tga                                                            2358
Pro
785

<210> SEQ ID NO 14
<211> LENGTH: 785
<212> TYPE: PRT
<213> ORGANISM: Homo sapiens

<400> SEQUENCE: 14

Met Asp Gly Phe Ala Gly Ser Leu Asp Asp Ser Ile Ser Ala Ala Ser
1               5                   10                  15

Thr Ser Asp Val Gln Asp Arg Leu Ser Ala Leu Glu Ser Arg Val Gln
            20                  25                  30

Gln Gln Glu Asp Glu Ile Thr Val Leu Lys Ala Ala Leu Ala Asp Val
        35                  40                  45

Leu Arg Arg Leu Ala Ile Ser Glu Asp His Val Ala Ser Val Lys Lys
    50                  55                  60

Ser Val Ser Ser Lys Gly Gln Pro Ser Pro Arg Ala Val Ile Pro Met
```

-continued

```
                65                  70                  75                  80
Ser Cys Ile Thr Asn Gly Ser Gly Ala Asn Arg Lys Pro Ser His Thr
                    85                  90                  95
Ser Ala Val Ser Ile Ala Gly Lys Glu Thr Leu Ser Ser Ala Ala Lys
                100                 105                 110
Ser Gly Thr Glu Lys Lys Glu Lys Pro Gln Gly Gln Arg Glu Lys
                115                 120                 125
Lys Glu Glu Ser His Ser Asn Asp Gln Ser Pro Gln Ile Arg Ala Ser
            130                 135                 140
Pro Ser Pro Gln Pro Ser Ser Gln Pro Leu Gln Ile His Arg Gln Thr
145                 150                 155                 160
Pro Glu Ser Lys Asn Ala Thr Pro Thr Lys Ser Ile Lys Arg Pro Ser
                165                 170                 175
Pro Ala Glu Lys Ser His Asn Ser Trp Glu Asn Ser Asp Asp Ser Arg
                180                 185                 190
Asn Lys Leu Ser Lys Ile Pro Ser Thr Pro Lys Leu Ile Pro Lys Val
            195                 200                 205
Thr Lys Thr Ala Asp Lys His Lys Asp Val Ile Ile Asn Gln Val Tyr
210                 215                 220
Arg Arg Lys His Gln Glu Leu Gln Ala Met Gln Met Glu Leu Gln Ser
225                 230                 235                 240
Pro Glu Tyr Lys Leu Ser Lys Leu Arg Thr Ser Thr Ile Met Thr Asp
                245                 250                 255
Tyr Asn Pro Asn Tyr Cys Phe Ala Gly Lys Thr Ser Ser Ile Ser Asp
                260                 265                 270
Leu Lys Glu Val Pro Arg Lys Asn Ile Thr Leu Ile Arg Gly Leu Gly
            275                 280                 285
His Gly Ala Phe Gly Glu Val Tyr Glu Gly Gln Val Ser Gly Met Pro
            290                 295                 300
Asn Asp Pro Ser Pro Leu Gln Val Ala Val Lys Thr Leu Pro Glu Val
305                 310                 315                 320
Cys Ser Glu Gln Asp Glu Leu Asp Phe Leu Met Glu Ala Leu Ile Ile
                325                 330                 335
Ser Lys Phe Asn His Gln Asn Ile Val Arg Cys Ile Gly Val Ser Leu
                340                 345                 350
Gln Ser Leu Pro Arg Phe Ile Leu Leu Glu Leu Met Ala Gly Gly Asp
            355                 360                 365
Leu Lys Ser Phe Leu Arg Glu Thr Arg Pro Arg Pro Ser Gln Pro Ser
            370                 375                 380
Ser Leu Ala Met Leu Asp Leu Leu His Val Ala Arg Asp Ile Ala Cys
385                 390                 395                 400
Gly Cys Gln Tyr Leu Glu Glu Asn His Phe Ile His Arg Asp Ile Ala
                405                 410                 415
Ala Arg Asn Cys Leu Leu Thr Cys Pro Gly Pro Gly Arg Val Ala Lys
                420                 425                 430
Ile Gly Asp Phe Gly Met Ala Arg Asp Ile Tyr Arg Ala Ser Tyr Tyr
            435                 440                 445
Arg Lys Gly Gly Cys Ala Met Leu Pro Val Lys Trp Met Pro Pro Glu
            450                 455                 460
Ala Phe Met Glu Gly Ile Phe Thr Ser Lys Thr Asp Thr Trp Ser Phe
465                 470                 475                 480
Gly Val Leu Leu Trp Glu Ile Phe Ser Leu Gly Tyr Met Pro Tyr Pro
                485                 490                 495
```

```
Ser Lys Ser Asn Gln Glu Val Leu Glu Phe Val Thr Ser Gly Gly Arg
            500                 505                 510

Met Asp Pro Pro Lys Asn Cys Pro Gly Pro Val Tyr Arg Ile Met Thr
            515                 520                 525

Gln Cys Trp Gln His Gln Pro Glu Asp Arg Pro Asn Phe Ala Ile Ile
            530                 535                 540

Leu Glu Arg Ile Glu Tyr Cys Thr Gln Asp Pro Asp Val Ile Asn Thr
545                 550                 555                 560

Ala Leu Pro Ile Glu Tyr Gly Pro Leu Val Glu Glu Glu Lys Val
            565                 570                 575

Pro Val Arg Pro Lys Asp Pro Glu Gly Val Pro Pro Leu Leu Val Ser
            580                 585                 590

Gln Gln Ala Lys Arg Glu Glu Arg Ser Pro Ala Ala Pro Pro Pro
            595                 600                 605

Leu Pro Thr Thr Ser Ser Gly Lys Ala Ala Lys Lys Pro Thr Ala Ala
    610                 615                 620

Glu Val Ser Val Arg Val Pro Arg Gly Pro Ala Val Glu Gly Gly His
625                 630                 635                 640

Val Asn Met Ala Phe Ser Gln Ser Asn Pro Pro Ser Glu Leu His Lys
            645                 650                 655

Val His Gly Ser Arg Asn Lys Pro Thr Ser Leu Trp Asn Pro Thr Tyr
            660                 665                 670

Gly Ser Trp Phe Thr Glu Lys Pro Thr Lys Lys Asn Asn Pro Ile Ala
            675                 680                 685

Lys Lys Glu Pro His Asp Arg Gly Asn Leu Gly Leu Glu Gly Ser Cys
    690                 695                 700

Thr Val Pro Pro Asn Val Ala Thr Gly Arg Leu Pro Gly Ala Ser Leu
705                 710                 715                 720

Leu Leu Glu Pro Ser Ser Leu Thr Ala Asn Met Lys Glu Val Pro Leu
            725                 730                 735

Phe Arg Leu Arg His Phe Pro Cys Gly Asn Val Asn Tyr Gly Tyr Gln
            740                 745                 750

Gln Gln Gly Leu Pro Leu Glu Ala Ala Thr Ala Pro Gly Ala Gly His
    755                 760                 765

Tyr Glu Asp Thr Ile Leu Lys Ser Lys Asn Ser Met Asn Gln Pro Gly
    770                 775                 780

Pro
785
```